(12) United States Patent
Ghulam Kadir et al.

(10) Patent No.: US 8,604,275 B2
(45) Date of Patent: Dec. 10, 2013

(54) CONSTITUTIVE TRANSLATIONALLY CONTROLLED TUMOR PROTEIN (TCTP) PROMOTER FROM OIL PALM TYPE 2

(75) Inventors: Ahmad Parveez Ghulam Kadir, Selangor (MY); Siti Masura Subhi, Selangor (MY); Leslie Eng Ti Low, Selangor (MY)

(73) Assignee: Malaysian Palm Oil Board, Kajang, Selangor (MY)

( * ) Notice: Subject to any disclaimer, the term of this patent is extended or adjusted under 35 U.S.C. 154(b) by 99 days.

(21) Appl. No.: 12/779,010

(22) Filed: May 12, 2010

(65) Prior Publication Data
US 2011/0173719 A1 Jul. 14, 2011

(30) Foreign Application Priority Data
May 13, 2009 (MY) .............................. PI 20091934

(51) Int. Cl.
*A01H 4/00* (2006.01)
*A01H 5/00* (2006.01)
*A01H 5/10* (2006.01)
*C12N 15/82* (2006.01)
*C12N 15/63* (2006.01)
*C12N 15/90* (2006.01)

(52) U.S. Cl.
USPC ........... 800/278; 800/279; 800/281; 800/284; 800/298; 800/300; 800/285; 800/295; 536/24.1; 536/23.6; 435/468; 435/419

(58) Field of Classification Search
None
See application file for complete search history.

(56) References Cited

U.S. PATENT DOCUMENTS

| | | | |
|---|---|---|---|
| 4,873,192 A | 10/1989 | Kunkel | |
| 4,945,050 A | 7/1990 | Sanford et al. | |
| 5,231,020 A | 7/1993 | Jorgensen et al. | |
| 5,316,931 A | 5/1994 | Donson et al. | |
| 5,366,892 A | 11/1994 | Foncerrada et al. | |
| 5,380,831 A | 1/1995 | Adang et al. | |
| 5,436,391 A | 7/1995 | Fujimoto et al. | |
| 5,563,055 A | 10/1996 | Townsend et al. | |
| 5,589,367 A | 12/1996 | Donson et al. | |
| 5,593,881 A | 1/1997 | Thompson et al. | |
| 5,602,321 A | 2/1997 | John | |
| 5,605,793 A | 2/1997 | Stemmer | |
| 5,723,756 A | 3/1998 | Peferoen et al. | |
| 5,737,514 A | 4/1998 | Stiffler | |
| 5,747,450 A | 5/1998 | Ohba et al. | |
| 5,792,931 A | 8/1998 | Duvick et al. | |
| 5,837,458 A | 11/1998 | Minshull et al. | |
| 5,866,785 A | 2/1999 | Donson et al. | |
| 5,879,918 A | 3/1999 | Tomes et al. | |
| 5,886,244 A | 3/1999 | Tomes et al. | |
| 5,889,190 A | 3/1999 | Donson et al. | |
| 5,889,191 A | 3/1999 | Turpen | |
| 5,932,782 A | 8/1999 | Bidney | |
| 5,981,840 A | 11/1999 | Zhao et al. | |
| 6,051,755 A * | 4/2000 | Zou et al. ................... 800/281 |
| 6,072,050 A | 6/2000 | Bowen et al. | |
| 6,506,559 B1 | 1/2003 | Fire et al. | |
| 6,518,484 B2 | 2/2003 | Kang et al. | |
| 6,545,202 B2 * | 4/2003 | Kang et al. ................. 800/317.3 |

OTHER PUBLICATIONS

Maniatis T et al. Molecular Cloning. A Laboratory Manual. 1982. pp. 387-389.*
Kim Y, Buckley K, Costa MA, and An G. A 20 nucleoide upstream element is essential for the nopaline synthase (nos) promoter activity. Plant Molecular Biology. 1994(24): pp. 105-117.*
Kennell DE. Principles and practices of nucleic acid hybridization. Progress in Nucleic Acid Research and Molecular Biology. 1971(11), pp. 259-301.*
Kim et al. A 20 nucleotide upstream element is essential for the nopaline synthase (nos) promoter activity. Plant Molecular Biology. 1994. 24: 105-117.*
Altschul et al., "Basic Local Alignment Search Tool," J. Mol. Biol., (1990), 215:403-410.
Altschul et al., "Gapped BLAST and PSI-BLAST: a new generation of protein database search programs," Nucleic Acids Res., (1997), 25:3389-3402.
Berkowitz et al, "Characterization of TCTP, the Translationally Controlled Tumor Protein, from *Arabidopsis thaliana*," The Plant Cell, (2008), 20:3430-3447.
Chowdhury et al, "Evaluation of five promoters for use in transformation of oil palm (*Elaeis guineensis* Jacq.)," Plant Cell Rep., (1997), 16:277-281.
Corpet et al, "Multiple sequence alignment with hierarchical clustering," Nucleic Acids Res., (1988), 16(22):10881-10890.
Doyle et al, "A rapid DNA isolation procedure for small quantities of fresh leaf tissue," Phytochemical Bulletin, (1987), 19(1):11-15.
Henikoff et al, "Amino acid substitution matrices from protein blocks," Proc. Natl. Acad. Sci USA, (1992) 89:10915-10919.
Higgins et al, "CLUSTAL: a package for performing multiple sequence alignment on a microcomputer," Gene, (1988), 73(1):237-244.
Higgins et al, "Fast and sensitive multiple sequence alignments on a microcomputer," Comput. Appl. Biosci., (1989), 5(2):151-153.
Huang et al, "Parallelization of a local similarity algorithm," CABIOS, (1992), 8(2):155-165.
Jones et al, "Isolation of the tomato Cf-9 gene for resistance to *Cladosporium fulvum* by transposon tagging," Science, (1994), 266:789-793.
Karlin et al, "Applications and statistics for multiple high-scoring segments in molecular sequences," Proc. Natl. Acad. Sci., (1993), 90:5873-5877.
Karlin et al, "Methods for assessing the statistical significance of molecular sequence features by using general scoring schemes," Proc. Natl. Acad. Sci.,(1990), 87:2264-2268.

(Continued)

*Primary Examiner* — Cathy Kingdon Worley
*Assistant Examiner* — Ashley K Buran
(74) *Attorney, Agent, or Firm* — Foley & Lardner LLP

(57) ABSTRACT

The present invention relates generally to a gene promoter from an oil palm plant and to a genetically modified plant comprising same. The gene promoter of the present invention is useful in facilitating expression of beneficial and/or desired phenotypic characteristics in plants and in particular oil palm plant products from such plants also form part of the present invention.

26 Claims, 8 Drawing Sheets

(56) References Cited

OTHER PUBLICATIONS

Klein et al, "High-velocity microprojectiles for delivering nucleic acids into living cells," Nature, (1987), 327:70-73.

Li et al., "Agronomic trait evaluation of field-grown transgenic rice plants containing the hygromycin resistance gene and the maize Activator element*1," Plant Science, (1995), 108(2):219-227.

Martin et al, "Map-based cloning of a protein kinase gene conferring disease resistance in tomato," Science, (1993), 262:1432-1436.

Mindrinos et al, "The *A. thaliana* disease resistance gene RPS2 encodes a protein containing a nucleotide-binding site and leucine-rich repeats," Cell, (1994), 78(6):1089-1099.

Murashige et al, "A Revised Medium for Rapid Growth and Bio Assay with Tobacco Tissue Cultures," Physiol. Plant., (1962), 15:473-497.

Myers et al, "Optimal alignments in linear space", CABIOS, (1988), 4(1):11-17.

Needleman et al., "A general method applicable of the search for similarities in the amino acid sequence of two proteins," J. Mol. Biol., (1970), 48:443-453.

Pearson et al, "Improved tools for biological sequence comparison," Proc. Natl. Acad. Sci., (1988), 85:2444-2448.

Pearson et al, "Using the FASTA program to search protein and DNA sequence database," Methods Mol. Biol., (1994), 24:307-331.

Rajanaidu et al, "World-wide performance of DXP planting materials and future prospects." In Proceedings of 1995 PORIM National Oil Palm Conference.—Technologies in Plantation, The Way Forward. 11-12 Julai, Kuala Lumpur: Palm Oil Research Institute of Malaysia, (1995), 1-29.

Ravigadevi et al, "Genetic Engineering of the Oil Palm," Malaysia Palm Oil Board, (2000), 1:284-331.

Sage-Ono et al, "Dark-induced accumulation of mRNA for a homolog of translationally controlled tumor protein (TCTP) in Pharbitis," Plant Cell Physiol., (1998), 39:357-360.

Shin D, Han Kyung-Hwan, "A *Hevea brasiliensis* Homolog of Translationally Controlled Tumor Protein (HevTCTP)(accession No. AF091455) Is Expressed Abundantly in Latex," (PGR 99-005). Plant Physiol., (1999), 119:363.

Smith et al., "Comparison of Biosequences," Advances in Applied Mathematics, (1981), 2(4):482-489.

Woo et al., "Cloning of genes whose expression is correlated with mitosis and localized in dividing cells in root caps of *Pisum sativum* L," Plant Mol. Biol., (1997), 35:1045-1051.

Zeng et al, "RNA Isolation From Highly Viscous Samples Rich in Polyphenols and Polysaccharides," Plant. Mol. Biol. Reporter, (2002), 20:417a-417e.

\* cited by examiner

```
  1 AAGTCCCGAT TGGATATTTC ATGAGATATC AAGATGAGTA TCATCTTATG TGTTAGGATA
                                                                 GATA
 61 GGATCATCCA GTTTAATCGG CACATCTTGA GATATTTTCT TATCTCAAGT ATCCAAATGA
    motif                            5'UTR Py-rich strech
121 GAGGAGATGA TGGTATATCT TGTTTCATTA GAAAATGAGG ATGGTACCTT CTTACAAGAT
      GAG motif                                         T      TCT motif
181 TTAAAGTCTT GGACCTAAAG TTGGATACCT AGATAAAGTG AGTTTGAGGA AATTAAAATG
                                                                  Gap
         HSE
241 GAGAAAAAAA TTTATGAGAG AAATTCCATA GATCCTATTC ATATTGGCAG CTACACTTAT
    Box
301 TCTTCCAAA TTTTTTCTCT CTGTTAACCA TAATTCATGC AGCCTCTCCA TTATCTTGCA
             5'UTR Py-rich strech
361 TCGACACTAG AGTACCGTGC AACATTTTTA TTGTAGTGTT ATCATTATCC TAGCGTCCAA
421 GAATTGGATT CAAAAGGCGT CTAAGCCCAT GGTAGTCCAT CCCCGAACTC GAACCAGACC
481 ATTTAGATTA GATCGGTTTT GGATTTGAGA CCTAATCATA ACAATCCGAT AAGAATTTGG
541 TCACCTGGAC TTCCGGTGTG AACATCTTTG AGATCAGAAT TCATCTCGCT GATCGGACGG
601 ACCGGAAAAG AGCTCGTGTG AAACTCGAAC ACCAACGATG GACTCAACTG TAGCCAGCGA
                                                       MBS
661 CACCCCGCTC GAAACCCCAA ATTCTCTCGC CCATATAAGA TCCTCGCGGC CACCTTTTA
                                           TATA box
721 GATCCCTCTC TCTCCTGCCT CCTTCGCCCG CTCCTTCGTC TATTCGGTCA CCGGGGGTTA
                         ***
781 GGGTTTGCTC TTTGGAGGAA TCATG
```

Figure 5

Embryogenic calli (EC)
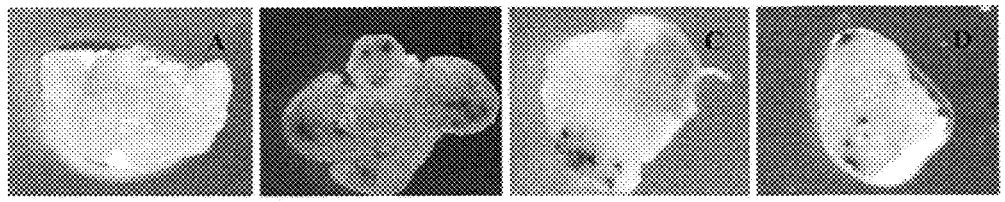
Embryoid
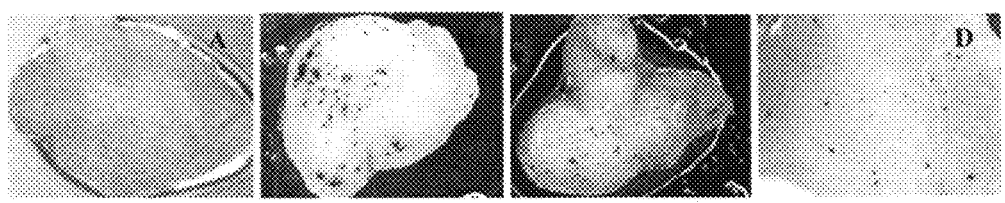
Young leaflet from mature palm (YMLP)
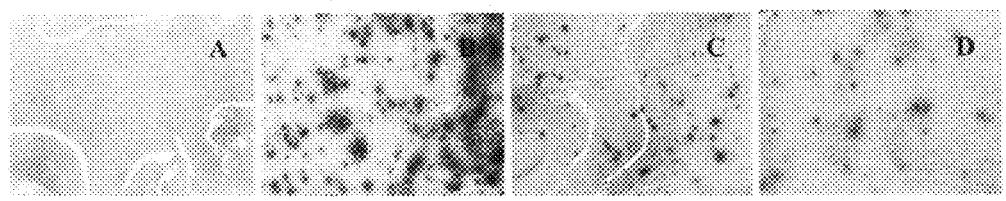
Green leaf
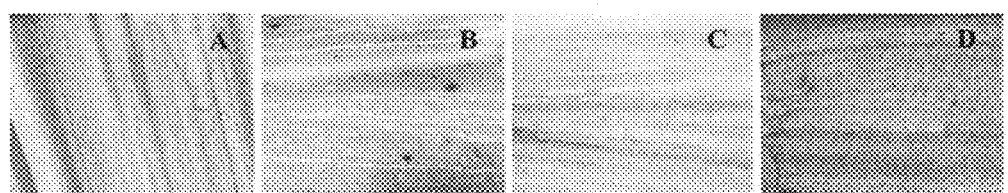
Figure 7a Mesocarp
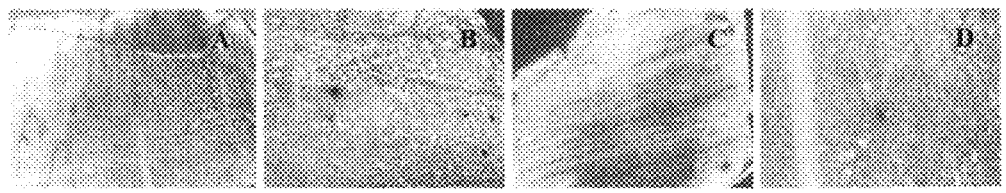
Stem/shoot tip
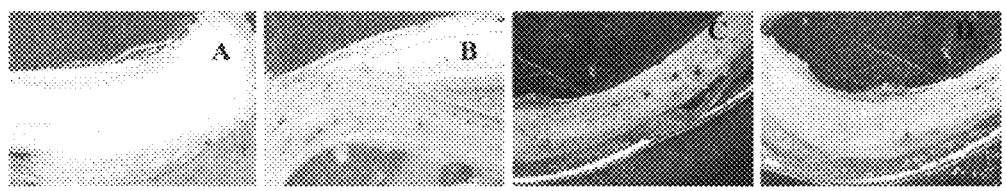
Immature embryo
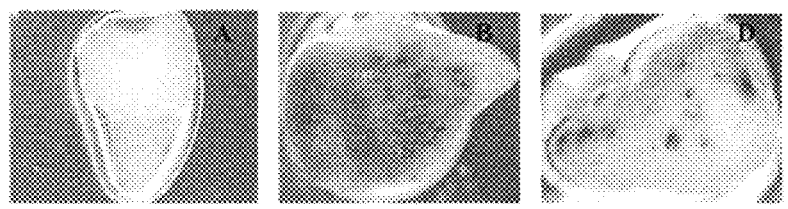
Figure 7b

CONSTITUTIVE TRANSLATIONALLY CONTROLLED TUMOR PROTEIN (TCTP) PROMOTER FROM OIL PALM TYPE 2

SEQUENCE LISTING

The instant application contains a Sequence Listing which has been submitted via EFS-Web and is hereby incorporated by reference in its entirety. Said ASCII copy, created on Aug. 20, 2010, is named 069359-1001.txt, and is 5,222 bytes in size.

CROSS-REFERENCE TO RELATED PATENT APPLICATIONS

This application claims the benefit of Malaysian Patent Application No. PI 20091934, filed May 13, 2009, which is incorporated herein by reference in its entirety and for all purposes.

FIELD

The present invention relates generally to a gene promoter from an oil palm plant and to a genetically modified plant comprising same. The gene promoter of the present invention is useful in facilitating expression of beneficial and/or desired phenotypic characteristics in plants and in particular oil palm plant products from such plants also form part of the present invention.

BACKGROUND

Reference to any prior art in this specification is not, and should not be taken as, an acknowledgement or any form of suggestion that this prior art forms part of the common general knowledge in Malaysia or any other country.

Bibliographic details of the publications referred to by author in this specification are collected at the end of the description.

The demand for oils and fats is expected to increase dramatically with the increase in world population and the need for sustainable resources. Oil palm plants, *Elaeis guineensis* and *Elaeis oleifera*, produce palm oil and palm kernel oil and represent the highest yielding oil crop in the world. Palm oil has been forecasted to contribute to around a quarter of the world's oil and fats demand by the year 2020 (Rajanaidu and Jalani, World-wide performance of DXP planting materials and future prospects. *In Proceedings of* 1995 *PORIM National Oil Palm Conference.—Technologies in Plantation*, The Way Forward. 11-12 Julai, Kuala Lumpur: Palm Oil Research Institute of Malaysia:1-29, 1995). Due to the demand, there is a need to increase the quality and yield of palm oil and palm kernel oil and to rapidly develop new characteristics when required.

Oil palm is the most important commercial crop in Malaysia. It has been identified as the most likely candidate for the development of a large scale production and renewal plant (Ravigadevi et al, Genetic engineering in oil palm. *In Advances in Oil Palm Research.* (eds). Yusof, Jalani, and Chan *Malaysia Palm Oil Board.* 1:284-331, 2000) for palm oil-derived chemicals. The ultimate aim is to genetically engineer the oil palm so as to modify its oil composition in order to expand its applicability. Moreover, the advancement in the genetic transformation of plants has made it possible to transfer foreign genes into the genome of oil palm (Parveez, PhD. Thesis. Universiti Putra Malaysia, 1998). Introduction of foreign genes via genetic engineering would potentially enhance the productivity and value of oil palm.

Genetic engineering can be used to improve plant quality by introducing and expressing selected genes into the plant genome. Genetic engineering processes are often unique to particular plants. An efficient tissue culture system is required in order to produce genetically modified plants after successful delivery and integration of genetic material into cells which regenerate into a whole plant. The introduced genetic material needs to be present in all cells of the regenerated plant and its progeny. The expression of the genetic material is controlled by promoters which may be constitutive or inducible, and operable ubiquitously in all plant cells or operable in a tissue specific manner.

A promoter is a short DNA sequence, usually upstream (5') to the relevant coding sequence, to which RNA polymerase binds before initiating transcription. This binding aligns the RNA polymerase so that transcription will initiate at a specific site. The nucleotide sequence of the promoter determines the nature of the enzyme that attaches to it and the rate of RNA synthesis. The RNA is processed to produce messenger RNA (mRNA) which serves as a template for translation of the RNA sequence into the amino acid sequence of the encoded polypeptide. The 5' non-translated leader sequence is a region of the mRNA upstream of the coding region that may play a role in initiation and translation of the mRNA. The 3' transcription termination/polyadenylation signal is a non-translated region downstream of the coding region that functions in the plant cells to cause termination of the RNA and the addition of polyadenylate nucleotides to the 3' end. It has been shown that certain promoters are able to direct RNA synthesis at a higher rate than others.

In order to functionally express a gene in plant, the transgene must have a promoter that is recognized by RNA polymerase in plant cells. There are two major classes of promoter, constitutive and regulated (or inducible). Constitutive promoters direct expression in virtually all tissues and are largely, if not entirely, independent of environmental and developmental factors. As their expression is normally not conditioned by endogenous factors, constitutive promoters are usually active across species and even across kingdoms. Tissue-specific or development-stage-specific promoters (regulated) direct the expression of a gene in specific tissue(s) or at certain stages of development. For plants, promoter elements that are expressed or affect the expression of genes in the vascular system, photosynthetic tissues, tubers, roots and other vegetative organs, or seeds and other reproductive organs can be found in heterologous systems (e.g. distantly related species or even other kingdoms) but the most specificity is generally achieved with homologous promoters (i.e. from the same species, genus or family). This is probably because the coordinate expression of transcription factors is necessary for regulation of the promoter's activity.

Because promoters affect transcription both quantitatively and qualitatively, the success of gene transfer technologies, varying from basic research to crop improvement and biopharming, depends on their efficacious selection and use (Potenza et al, *In Vitro Cell. Dev. Biol. Plant* 40:1-22, 2004). Plant promoters that are capable of driving high and constitutive expression of a particular transgene have become a valuable tool in plant genetic engineering. These promoters are required to select transgenic cells or plants that have a high level of production of the specific protein of interest. The high expression of a selectable marker is important to identify a non-transformed cell and to enable selection of a resistant transformant which will survive and generate into transgenic plant (Parveez, 1998, supra). This prevents non-transformant domination of the culture and promotes the growth of chimeric plants (Christou, *The Plant J.* 2:275-281, 1992; Ritala et al, *Plant Mol. Biol.* 24:317-325, 1994). The high level expression of a reporter protein such as GUS, GFP and CAT in a plant cell can also be achieved by using constitutive promoters. Moreover, the use of constitutive promoters is essential in the production of compounds that require ubiquitous activity in the plant and during all stages of plant development.

There are diverse spectra of constitutive promoters which are available for use in the genetic engineering of plants (Xiao et al, *Molecular Breeding,* 15:221-231, 2005). A commonly used example which results in the strong constitutive expression of a transgene in a plant is the CaMV35S promoter which originates from the cauliflower mosaic virus (Potenza et al, 2004 supra). Additionally, it has been reported that a number of widely used constitutive promoters include maize ubiquitin (Christensen and Quail, *Transgenic Research* 5:213-218, 1996), rice Actin 1 (McElroy et al, *Plant Cell.* 2:163-171, 1990) and maize derived Emu (Last et al, *Theor. Appl. Genet.,* 81:581-588, 1991). Although a number of constitutive promoters have been isolated, it is still important to identify new plant promoters, especially for the high level expression of transgenes or other genetic material in selected plants or selected parts of plants. A wider range of effective promoters would make it possible to introduce multiple transgenes into plant cells while avoiding the risk of homology-dependent gene silencing (Xiao et al, 2005 supra).

As in other genetically engineered plants, constitutive promoters have previously been used to drive the expression of genes in transgenic oil palms. The promoters, Emu and Ubi1, were found to be the most efficient promoters in driving high level expression of foreign genes in oil palm plants (Chowdhury et al, *Plant Cell Rep.:*16:277-82, 1997). However, these promoters originated from unrelated plant species. Previous studies have shown that promoters can be more effective if isolated from the same species as the transgenic plant. McElroy et al, 1990 supra found, for example that β-glucuronidase (GUS) expression under the control of a rice actin promoter (Act1) in transformed rice protoplasts was approximately 6-fold greater than expression induced under the control of the maize Adh1 promoter.

There is a need to identify promoters derived from the oil palm genome to facilitate genetic manipulation of oil palm plants as well as other plant species.

SUMMARY

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:1 and SEQ ID NO:2, etc which corresponst to the equivalent designations <400> 1, <400> 2, respectively). A summary of the sequence identifiers is provided in Table 1. A sequence listing is provided after the claims.

The present invention provides a promoter for use in the genetic manipulation of plants and more particularly oil palm plants of the species *Elaeis*. The promoter of the present invention is referred to as the "*Elaeis* TCTP promoter" or the "*Elaeis* Translationally Controlled tumor" promoter and is isolatable from *Elaeis* sp. Reference to the "*Elaeis* TCTP promoter" includes the TCTP promoter itself as well as functional homologs, derivatives and equivalents thereof. The "*Elaeis* TCTP promoter" may also be referred to as the "oil palm promoter" In accordance with the present invention, oil palm plants comprising the *Elaeis* TCTP promoter operably linked to genetic material constitutively express the genetic material to produce mRNA or other RNA species or peptides, polypeptides or proteins. The genetic material may, for example, confer resistance to a herbicide, resistance to a plant pest including a virus, insect, fungus or microbe, confer a defense to a disease condition, or the genetic material may modify lipids and non-lipid components of palm oil resulting in improved quality of palm oil or altered or improved production of industrial oils and chemicals. The genetic material may also encode nutraceutical or pharmaceutical molecules. The *Elaeis* TCTP promoter may be used in a range of plants in addition to *Elaeis* sp.

Accordingly, one aspect of the present invention is an isolated nucleic acid molecule comprising an *Elaeis* TCTP promoter or a functional homolog, derivative or equivalent thereof.

Another aspect of the present invention provides a method for the generation of a DNA construct comprising an *Elaeis* TCTP promoter operably linked or linkable to a heterologous nucleic sequence of interest. The method comprises introducing into a plasmid an *Elaeis* TCTP promoter and either a heterologous nucleic acid sequence operably linked thereto or restriction endonuclease means to insert a heterologous sequence.

A particular aspect of the present invention contemplates a method for expressing a nucleotide sequence in a plant or a parent of such a plant, the method comprising introducing into a plant a DNA construct, the DNA construct comprising an *Elaeis* TCTP promoter operably linked to a heterologous nucleotide sequence of interest.

Yet another aspect of the present invention provides a method for expressing a nucleotide sequence in a plant cell, the method comprising introducing into a plant cell or parent of such a plant cell a DNA construct comprising an *Elaeis* TCTP promoter operably linked to a heterologous nucleotide sequence of interest.

Still another aspect of the present invention contemplates a method of genetically modifying a plant whereby a heterologous nucleotide sequence encoding a proteinaceous product or double-stranded RNA or other RNA species which confers resistance to a herbicide, resistance to a pest including a pathogenic agent or confers a defense to a disease condition, or which confers a modification lipids and non-lipid components of palm oil is expressed, the method comprising introducing the heterologous nucleotide sequence operably linked to an *Elaeis* TCTP promoter into a cell of a plant, regenerating a plant from the cell wherein the regenerated plant and its progeny are genetically modified.

Yet another aspect the present invention is directed to for the use of an *Elaeis* TCTP promoter in the generation of a genetically modified plant or its progeny or products therefrom.

Reference to an "*Elaeis* TCTP promoter" includes a functional homolog, derivative or equivalent thereof, comprising a nucleotide sequence expressible in *Elaeis* species selected from a nucleotide sequence set forth in SEQ ID NO:1 or a complement thereof; or a nucleotide sequence comprising a sequence having at least 70% sequence identity to the sequence set forth in SEQ ID NO:1 or a nucleotide sequence which hybridizes to SEQ ID NO:1; or complement thereof under low stringency conditions and which promoter initiates transcription in a plant cell.

The present invention is directed, therefore, to an isolated nucleic acid molecule, comprising a promoter from the gene encoding *Elaeis* TCTP, the promoter comprising a nucleotide sequence selected from the group consisting of a nucleotide sequence set forth in SEQ ID NO:1 or a complement thereof; or a nucleotide sequence comprising a sequence having at least 70% sequence identity to the sequence set forth in SEQ ID NO:1; or a nucleotide sequence which hybridizes to SEQ ID NO:1 or complement thereof under low stringency conditions and which promoter initiates transcription in a plant cell.

In a particular embodiment, the present invention provides an isolated nucleic acid molecule comprising the nucleotide sequence set forth in SEQ ID NO:1 or sequence having at least 70% identity thereto or which hybridizes to SEQ ID NO:1 or a complement thereof under low stringency conditions and which nucleic acid molecule functions as a promoter of a cell of an *Elaeis* species.

Another aspect of the present invention contemplates homolog of the TCTP promoter comprising a promoter region in a gene which comprises a nucleotide sequence encoding an amino acid sequence having at least 80% similarity to SEQ ID NO:4 or a nucleotide sequence having at least 70% identity to SEQ ID NO:2 or 3 or which hybridizes to SEQ ID NO:2 or 3 under low stringency conditions.

The term "*Elaeis* TCTP" refers to the gene encoding Translationally Controlled Tumor Protein from an *Elaeis* sp. The promoter associated with this gene is the "*Elaeis* TCTP promoter". Reference to "*Elaeis* sp" includes *Elaeis* guineensis and *Elaeis* oleifera.

Whilst the *Elaeis* TCTP promoter of the present invention is particularly useful in the genetic manipulation of *Elaeis* species, the present invention extends to its use in a range of plants including crop plants, ornamental flowering plants and other plant types. Hence, another aspect of the present invention is directed to a genetically modified plant comprising a TCTP promoter operably linked to a heterologous nucleotide sequence which upon expression conferred a desired trait on the plant or its progeny or in a product of the plant.

In a particular embodiment, the plant is an oil palm plant and the product is oil palm.

Functional fragments, truncates, insertates of the *Elaeis* TCTP promoter is encompassed by the present invention which are included in the term "derivatives".

A summary of the sequence identifier referred to herein is in Table 1.

TABLE 1

Summary of sequence identifier

| SEQ ID NO | DESCRIPTION |
| --- | --- |
| 1 | Nucleotide sequence of Translationally Controlled Tumor Protein (TCTP) gene promoter region from *Elaeis guineensis* |
| 2 | Nucleotide sequence of coding strand and 3' end of TCTP gene from *Elaeis guineensis* |
| 3 | Nucleotide sequence of complementary strand of SEQ ID NO: 2 |
| 4 | Amino acid sequence of TCTP from *Elaeis guineensis* |

BRIEF DESCRIPTION OF THE FIGURES

FIG. 5 is a schematic representation of nucleotide sequences and putative motifs of the oil palm TCTP promoter and corresponds to SEQ ID NO: 1 plus the start codon. The start codon of the TCTP gene is indicated with bold font and asterisks. Position of transcription start site is indicated with large and bold font. The putative TATA box and other putative motifs are underlined and labeled.

FIGS. 7a and 7b are photographic representations showing a comparison of transient histochemical gus A gene expression in various oil palm tissues after bombardment with plasmid carrying different promoters. A) none (bombarded without plasmid DNA); B) pAHC25 (Ubil); C) pBI221 (CaMV35S); and D) pTCTP (TCTP). For immature embryo, the tissue was not bombarded with pBI221 because of limited sample.

DETAILED DESCRIPTION

Figure 1:
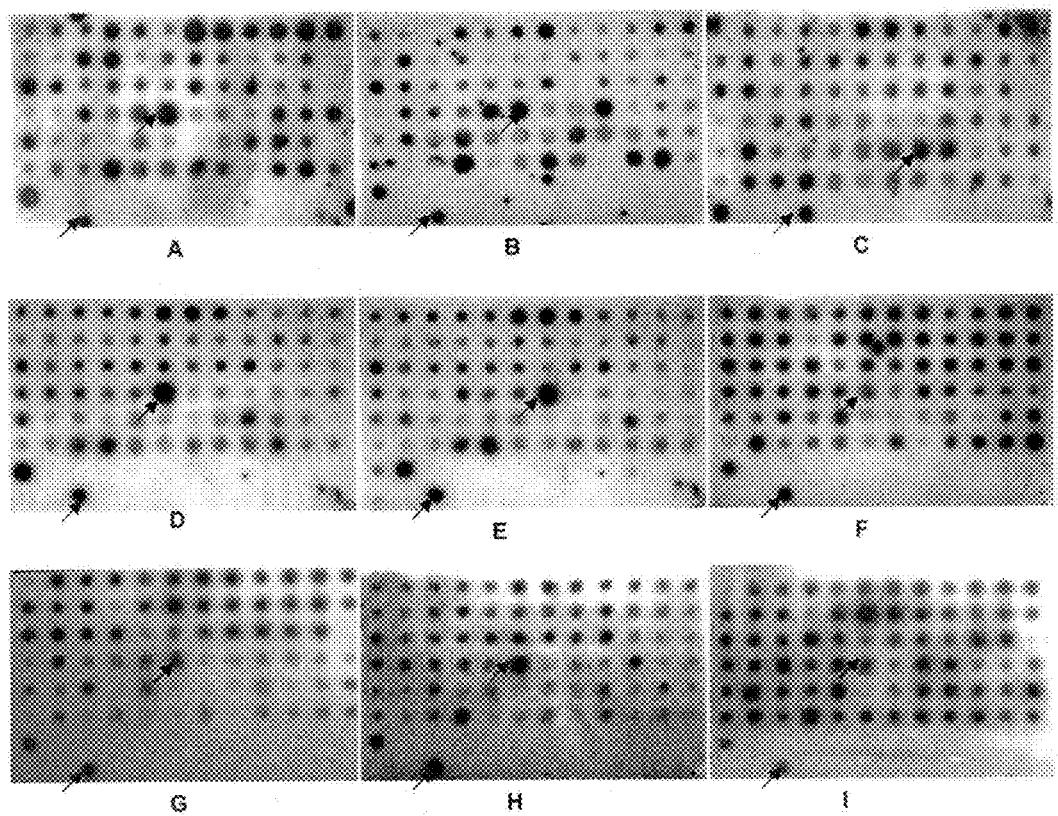
FIG. 1 is a photographic representation showing reverse northern analysis to screen expression pattern of 73 cDNA clone analyzed through microarray approach. The membranes were hybridized with first strand cDNA from A) mesocarp 5 week after anthesis (WAA); B) mesocarp 9 WAA; C) mesocarp 14 WAA; D) mesocarp 15 WAA; E) mesocarp 17 WAA; F) kernel 14 WAA; G) kernel 17 WAA; H) frond and I) flower. Blue and red arrows indicate location of pOP-RD00041 clone and ribosomal DNA, respectively.

The present invention is directed to an isolated nucleic acid molecule which defines a constitutive promoter, the Translationally Controlled Tumor Protein (TCTP) gene promoter), from a species of *Elaeis* (*Elaeis* TCTP promoter or oil palm promoter) and to the generation of plasmid constructs and genetically modified plants comprising the *Elaeis* TCTP promoter and products from such genetically modified plants and their progeny.

The ability to produce genetically modified plants such as oil palm plants with the *Elaeis* TCTP promoter operably linked to particular genetic material facilitates the further improvement or modification of plants. For example, in relation to oil plants introduction of useful traits include, for example, plants which exhibit increased yield of oil, are resistant to certain diseases including those caused by pathogenic agents, have modified lipids and non-lipid components of palm oil and improved quality of palm oil or improved production of industrial oils and chemicals. The traits may also include the production of nutraceutical and pharmaceutical compounds.

Embodiments of the present invention are predicated in part on the identification of the constitutive promoter, the TCTP promoter, from *Elaeis* species which facilitates expression of genetic material which is operably linked to the promoter. The TCTP promoter is defined as a nucleotide sequence set forth in SEQ ID NO:1 or a complement thereof; or a nucleotide sequence comprising a sequence having at least 85% sequence identity to the sequence set forth in SEQ ID NO:1; or a nucleotide sequence which hybridizes to SEQ ID NO:1 or complement thereof under low stringency conditions and which initiates transcription in a plant cell. Such a promoter may be a functional derivative such as a fragment truncate or insertate of the *Elaeis* TCTP promoter or a novel homolog from another plant or microorganism which is operable in an *Elaeis* sp.

The open reading frame for the TCTP gene is set forth in SEQ ID NO:2 (with a 3' non-coding region) [and a complementary sequence set forth in SEQ ID NO:3] and the amino acid sequence corresponding to SEQ ID NO:2 is set forth in SEQ ID NO:4.

The present invention extends, therefore, to a promoter region from a homologous gene having a nucleotide sequence encoding an amino acid sequence having at least 80% similarity to SEQ ID NO:4 or at least 70% identity to SEQ ID NO:2 or 3 or which hybridizes to SEQ ID NO:2 or 3 under low stringency conditions. Accordingly, another aspect of the present invention contemplates homolog of the TCTP promoter comprising a promoter region in a gene which comprises a nucleotide sequence encoding an amino acid sequence having at least 80% similarity to SEQ ID NO:4 or a nucleotide sequence having at least 70% identity to SEQ ID NO:2 or 3 or which hybridizes to SEQ ID NO:2 or 3 under low stringency conditions.

A homolog of the TCTP promoter includes a nucleotide sequence having at least 70% identity to SEQ ID NO:1 or which hybridizes to SEQ ID NO:1 or its complementary form under low stringency conditions.

The promoter sequence of the present invention is useful for expressing operably linked or linkable nucleotide sequences in a constitutive manner in a range of plants including species of *Elaeis*. The sequences also find use in the construction of expression vectors for subsequent transformation into plants of interest, as probes for the isolation of other gene promoters, as molecular markers, and the like. The TCTP promoter of the present invention was isolated from the oil palm plant, *Elaeis* sp. The specific method used to obtain the TCTP promoter of the present invention is described in the Examples in this specification.

Hence, one aspect of the present invention is directed to the isolation of a nucleic acid molecule comprising a constitutive *Elaeis* TCTP promoter or a functional homolog, derivative or equivalent thereof. For brevity, reference to the "*Elaeis* TCTP promoter" includes reference to its functional homologs, derivatives and equivalents. Having said that, in a particular embodiment, the present invention provides an isolated nucleic acid molecule comprising a TCTP promoter from *Elaeis* species. A derivative includes a functional fragment, truncate or insertate. It also includes an *Elaeis* TCTP promoter with single or multiple nucleotide substitutions, deletions and/or additions.

This embodiment encompasses isolated or substantially purified nucleic acid compositions. An "isolated" or "purified" nucleic acid molecule, or biologically active portion thereof, is substantially free of other cellular material or culture medium when produced by recombinant techniques, or substantially free of chemical precursors or other chemicals when chemically synthesized. An "isolated" nucleic acid is substantially free of sequences (including protein encoding sequences) that naturally flank the nucleic acid (i.e., sequences located at the 5' and 3' ends of the nucleic acid) in the genomic DNA of the *Elaeis* species. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

Another aspect of the present invention contemplates a method for expressing a nucleotide sequence in a plant and/or plant cell, the method comprising introducing in a plant and/or plant cell or a parent of the plant or plant cell, a DNA construct, comprising an *Elaeis* TCTP promoter operably linked to a heterologous nucleotide sequence of interest.

As used herein, the term "construct" and/or "vector" and/or "plasmid" refers to a nucleic acid molecule capable of carrying another nucleic acid to which it has been linked or inserted. Particular vectors are those capable of expression of nucleic acids contained within. Vectors capable of directing the expression of genetic material to which they are operatively linked are referred to herein as "expression vectors." In general, expression vectors of utility in recombinant DNA techniques are often in the form of "plasmids" which refer generally to circular double stranded DNA loops which, in their vector form, are not bound to the chromosome. In the present specification, "plasmid" and "vector" are used interchangeably. In particular, the plasmid or vector comprises the *Elaeis* TCTP promoter and either a heterologous nucleotide sequence operably linked thereto or restriction endonuclease means to insert a heterologous nucleotide sequence in operable linkage to the *Elaeis* TCTP promoter. By "restriction endonuclease means" is meant one or more restriction endonuclease sites which can be used to linearize a covalently closed circular plasmid in order to re-ligate in the presence of a heterologous nucleotide sequence such that the heterologous nucleotide sequence is operably linked to the *Elaeis* TCTP promoter.

The term "genetic material" includes a "gene" which is used in its broadest sense and encompasses cDNA corresponding to the exons of a gene. Accordingly, reference herein to a "gene" is to be taken to include:—

(i) a classical genomic gene consisting of transcriptional and/or translational regulatory sequences and/or a coding region and/or non-translated sequences (i.e. introns, 5'- and 3'-untranslated sequences);

(ii) mRNA or cDNA corresponding to the coding regions (i.e. exons) and 5'- and 3'-untranslated sequences of the gene; and/or (iii) genetic material which when transcribed gives rise to mRNA or other RNA species or after translation gives rise to a peptide, polypeptide or protein.

The term "genetic material" and "gene" is also used to describe synthetic or fusion molecules encoding all or part of a functional product. The term "genetic material" also encompasses a gene or such molecules as RNAi, ssRNA, dsRNA and the like.

The genetic material may be in the form of a genetic construct comprising a gene or nucleic acid molecule to be introduced into a plant cell operably linked to an *Elaeis* TCTP promoter and optionally operably linked to various regulatory sequences.

The genetic material of the present invention may comprise a sequence of nucleotides or be complementary to a sequence of nucleotides which comprise one or more of the following: a promoter sequence, a 5' non-coding region, a cis-regulatory region such as a functional binding site for transcriptional regulatory protein or translational regulatory protein, an upstream activator sequence, an enhancer element, a silencer element, a TATA box motif, a CCAAT box motif, or an upstream open reading frame, transcriptional start site, translational start site, and/or nucleotide sequence which encodes a leader sequence.

The term "5' non-coding region" is used herein in its broadest context to include all nucleotide sequences which are derived from the upstream region of an expressible gene, other than those sequences which encode amino acid residues which comprise the polypeptide product of said gene, wherein the 5' non-coding region confers or activates or otherwise facilitates, at least in part, expression of the gene. The TCTP promoter is contained within the 5' non-coding region of the genomic gene encoding TCTP. The nucleotide sequence encompassing the *Elaeis* TCTP promoter is set forth in SEQ ID NO:1.

The *Elaeis* TCTP promoter is constitutively expressed in *Elaeis* tissue and its expression was identified by screening the expression pattern of EST clones by using reverse northern analysis, northern analysis and DNA sequencing experiments which are further disclosed in the Examples. The TCTP promoter sequence directs expression of operably linked nucleotide sequences in all tissues. In *Elaeis* tissue, the TCTP promoter directs constitutive expression. However, the present invention extends to modified TCTP promoters which have become fully or partially inducible.

The present invention includes isolated nucleic acid molecules comprising the promoter nucleotide sequence set forth in SEQ ID NO:1. Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter expression of genetic material in response to developmental and/or environmental stimuli, or in a tissue-specific or cell-type-specific manner. An *Elaeis* TCTP promoter is usually, but not necessarily, positioned upstream or 5', of genetic material, the expression of which it regulates. This is referred to as the promoter being operably linked to a particular nucleotide sequence.

In the present context, the term *Elaeis* TCTP" or "oil palm promoter" is also used to describe a synthetic or fusion promoter molecule, or derivative thereof which confers, activates or enhances expression of genetic material.

The term "operably connected" or "operably linked" in the present context means placing a genetic material under the regulatory control of the *Elaeis* TCTP promoter which then controls expression of this material. The promoter is generally positioned 5' (upstream) to the genes which they control. As indicated above, in one embodiment, the *Elaeis* TCTP promoter functions constitutively.

The present invention extends to regulatory elements within the *Elaeis* TCTP promoter or added or incorporated therewith. In the context of this disclosure, the term "regulatory element" also refers to a sequence of DNA, either, upstream (5') or downstream (3') to the coding sequence of the genetic materials to be expressed, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements (as discussed elsewhere in this specification) that modify gene expression. It is to be understood that nucleotide sequences, located within introns or 3' of the coding region sequence also contribute to the regulation of expression of a coding region of interest. In the context of the present disclosure, a post-transcriptional regulatory element located 3' to the coding sequence may include elements that are active following transcription initiation, for example translational and transcriptional enhancers, translational and transcriptional repressors, and mRNA stability determinants.

The *Elaeis* TCTP promoter sequence, when assembled within a DNA construct such that the promoter is operably linked to a nucleotide sequence of interest, enables expression of the nucleotide sequence in the cells of a plant stably transformed with this DNA construct as well as progeny or relatives of these cells. As indicated above, the term "operably linked" is intended to mean that the transcription or translation of the heterologous nucleotide sequence is under the influence of the promoter sequence. "Operably linked" is also intended to mean the joining of two nucleotide sequences such that the coding sequence of each DNA fragment remains in the proper reading frame. In this manner, the nucleotide sequences for the *Elaeis* TCTP promoter of the present invention are provided in DNA constructs along with the nucleotide sequence of interest, typically a heterologous nucleotide sequence, for expression in the plant of interest. The term "heterologous nucleotide sequence" is intended to mean a sequence that is not naturally operably linked with the *Elaeis* TCTP promoter sequence. While this nucleotide sequence is heterologous to the promoter sequence, it may be homologous or native; or heterologous or foreign, to the plant host. It is recognized that the TCTP promoter of the present invention may be used with its native coding sequences to increase or decrease expression, thereby resulting in a change in phenotype of the transformed plant. For example, the TCTP gene sequence or part thereof may be fused at the 5' or 3' end to another sequence.

Modifications of the isolated *Elaeis* TCTP promoter sequences of the present invention can provide for a range of expression of the heterologous nucleotide sequence. Fragments and variants of the TCTP promoter sequences are also encompassed by the present invention. A "fragment" is intended to mean a portion of the promoter sequence. Fragments of a promoter sequence may retain biological activity and hence encompass fragments capable of driving inducible expression of an operably linked nucleotide sequence. Thus, for example, less than the entire promoter sequence disclosed herein may be utilized to drive expression of an operably linked nucleotide sequence of interest, such as a nucleotide sequence encoding a heterologous protein or an RNA species.

Those skilled in the art are able to determine whether such fragments decrease expression levels or alter the nature of expression, e.g. from constitutive to inducible expression. Alternatively, fragments of a promoter nucleotide sequence that is useful as hybridization probes, such as described below, may not retain this regulatory activity. Thus, fragments of a nucleotide sequence may range from at least about 20 nucleotides, about 50 nucleotides, about 100 nucleotides, about 500 nucleotides, about 1000 nucleotides and up to the full-length nucleotide sequence of the *Elaeis* TCTP promoter.

Thus, a fragment of an *Elaeis* TCTP promoter nucleotide sequence may comprise a biologically active portion or it may be a fragment that can be used as a hybridization probe or PCR primer to identify homolog promoters or to screen for the presence of the TCTP promoter. A biologically active portion of the TCTP promoter can be prepared by isolating a portion of the TCTP promoter nucleotide sequence and assessing the activity of that portion of the TCTP promoter.

The nucleotides of such fragments usually comprise the TATA recognition sequence of the particular promoter sequence. Such fragments may be obtained by use of restriction enzymes to cleave the naturally occurring promoter nucleotide sequence disclosed herein; by synthesizing a nucleotide sequence from the naturally occurring sequence of the promoter DNA sequence; or may be obtained through the use of PCR technology. See particularly, Mullis et al, *Methods Enzymol.* 55:335-350, 1987, and Erlich, ed. PCR Technology (Stockton Press, New York, 1989). Variants of these promoter fragments, such as those resulting from site-directed mutagenesis and a procedure such as DNA "shuffling", are also encompassed by the compositions of the embodiments. An "analog" of the regulatory elements of the embodiments includes any substitution, deletion, or addition to the sequence of a regulatory element provided that said analog maintains at least one regulatory property associated with the activity of the regulatory element of the embodiments.

The term "variants" is intended to mean sequences having substantial similarity with a promoter sequence disclosed herein. For nucleotide sequences, naturally occurring variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the embodiments will have at least 40%, 50%, 60%, 65%, 70%, 75%, 80%, 85%, 90%, 91%, 92%, 93%, 94%, to 95%, 96%, 97%, 98%, or 99% or more sequence identity to that particular nucleotide sequence as determined by sequence alignment programs described elsewhere herein using default parameters. Biologically active variants are also encompassed by the embodiments. Biologically active variants include, for example, the native promoter sequences of the embodiments having one or more nucleotide substitutions, deletions, or insertions. Promoter activity may be measured by using techniques such as Northern blot analysis, reporter activity measurements taken from transcriptional fusions, and the like. See, for example, Sambrook et al, (*Molecular Cloning: A Laboratory Manual* (2d ed., Cold Spring Harbor Laboratory Press, Cold Spring Harbor, N.Y., 1989), hereinafter "Sambrook," herein incorporated by reference. Alternatively, levels of a reporter gene such as green fluorescent protein (GFP) or the like produced under the control of a promoter fragment or variant can be measured. See, for example, U.S. Pat. No. 6,072,050.

Methods for mutagenesis and nucleotide sequence alterations are well known in the art. See, for example, Kunkel, *Proc. Natl. Acad. Sci.* USA 82:488-492, 1985; Kunkel et al, *Methods in Enzymol.* 54:367-382, 1987; U.S. Pat. No. 4,873,192; Walker and Gaastra, eds., *Techniques in Molecular Biology*, MacMillan Publishing Company, New York, 1983 and the references cited therein. Variant promoter nucleotide sequences also encompass sequences derived from a mutagenic and recombinogenic procedure such as DNA shuffling. With such a procedure, one or more different promoter sequences can be manipulated to create a new promoter possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer, *Proc. Natl. Acad. Sci.* USA 91:10747-10751, 1994; Stemmer, *Nature* 370:389-391, 1994; Crameri et al, *Nature Biotech.* 15:436-438, 1997; Moore et al, *J. Mol. Biol.* 272:336-347, 1997; Zhang et al, *Proc. Natl. Acad.* Sci. USA 94:4504-4509, 1997; Crameri et al, *Nature* 391:288-291, 1998; and U.S. Pat. Nos. 5,605,793 and 5,837,458.

The *Elaeis* TCTP promoter sequence of the present invention can be used to isolate corresponding sequences from other organisms, such as other plants, for example, other monocots. Such a TCTP promoter is a homolog of an *Elaeis* TCTP promoter. In this manner, methods such as PCR, hybridization, and the like can be used to identify such sequences based on their sequence homology to the sequence set forth herein. Sequences isolated based on their sequence identity to the entire TCTP promoter sequence set forth herein or to fragments thereof are encompassed by the embodiments. The promoter regions of the present invention may be isolated from any plant, including, but not limited to corn (*Zea mays*), Brassica (*Brassica napus, Brassica rapa*), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats, barley, safflower, vegetables, ornamentals, and conifers. Novel homologs of an *Elaeis* TCTP promoter are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook, 1989 supra. See also Innis et al, eds. *PCR Protocols: A Guide to Methods and Applications* (Academic Press, New York), 1990; Innis and Gelfand, eds. *PCR Strategies* (Academic Press, New York), 1995; and Innis and Gelfand, eds. *PCR Methods Manual* (Academic Press, New York), 1999. Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the TCTP promoter sequence. Methods for preparation of probes for hybridization and for construction of cDNA and genomic libraries are generally known in the art and are disclosed in Sambrook, 1989 supra.

For example, the entire TCTP promoter sequence disclosed herein, or one or more portions thereof, may be used as a probe capable of specifically hybridizing to corresponding (homolog or variant) TCTP promoter sequences. To achieve specific hybridization under a variety of conditions, such probes include sequences that are unique among TCTP promoter sequences and are generally at least about 10 nucleotides in length, including sequences of at least about 20 nucleotides in length including at least 30 nucleotides in length including large fragments or a full length promoter. Such probes may be used to amplify corresponding TCTP promoter sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook supra). Hybridization of such sequences may be carried out under stringent conditions. "Stringent conditions" or "stringent hybridization conditions" are conditions under which a probe will hybridize to its target sequence to a detectably greater degree than to other sequences (e.g., at least two-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing).

Typically, stringent conditions will be those in which the salt concentration is less than about 1.5M Na ion, typically about 0.01 to 1.0M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% v/v formamide, 1M NaCl, 1% w/v SDS (sodium dodecyl sulphate) at 37° C., and a wash in 1× to 2×SSC (2×SSC=3.0 M NaCl/0.3 M trisodium citrate) at 50 to 55° C. Exemplary moderate stringency conditions include hybridization in 40 to 45% v/v formamide, 1.0M NaCl, 1% w/v SDS at 37° C., and a wash in 0.5× to 1×SSC at 55 to 60° C. Exemplary high stringency conditions include hybridization in 50% v/v formamide, 1M NaCl, 1% w/v SDS at 37° C., and a final wash in 0.1×SSC at 60 to 65° C. for at least 30 minutes. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl, *Anal. Biochem,* 38:267-284, 1984: $T_m$=81.5° C.+16.6 (log M)+0.41 (% GC)−0.61 (% GC)−(% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the Tm for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes, Part II Chapter* 2 (Elsevier, N.Y.), 1993; and Ausubel et al, eds. *Current Protocols in Molecular Biology,* Chapter 2 (Greene Publishing and Wiley-Interscience, New York), 1995, hereinafter "Ausubel". See also Sambrook, 1989 supra.

Thus, isolated sequences that have promoter activity and which hybridize under stringent conditions to the *Elaeis* TCTP promoter sequences disclosed herein, or to fragments thereof, are encompassed by the embodiments.

In general, sequences that have promoter activity and hybridize to the *Elaeis* TCTP promoter sequence disclosed herein have at least 40% to 50% homology, about 60%, 70%, 80%, 85%, 90%, 95% to 98% homology or more with the disclosed TCTP promoter sequences. That is, the sequence similarity of sequences may range, sharing at least about 40% to 50%, about 60% to 70%, and about 80%, 85%, 90%, 95% to 98% sequence similarity. The following terms are used to describe the sequence relationships between two or more nucleic acids or polynucleotides: (a) "reference sequence", (b) "comparison window", (c) "sequence identity", (d) "percentage of sequence identity", and (e) "substantial identity".

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller, *CABIOS* 4:11-17, 1988; the local homology algorithm of Smith et al, *Adv. Appl. Math.* 2:482, 1981; the homology alignment algorithm of Needleman and Wunsch, *J. Mol. Biol.* 48:443-453, 1970; the algorithm of Pearson and Lipman, *Proc. Natl. Acad. Sci* 85:2444-2448, 1988; the algorithm of Karlin and Altschul, *Proc. Natl. Acad. Sci.* USA 87:2264, 1990, modified as in Karlin and Altschul, *Proc. Natl. Acad. Sci* USA 90:5873-5877, 1993.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0); the ALIGN PLUS program (Version 3.0, copyright 1997): and GAP, BESTFIT, BLAST, FASTA, and TFASTA in the Wisconsin Genetics Software Package of Genetics Computer Group, Version 10 (available from Accelrys, 9685 Scranton Road, San Diego, Calif., 92121, USA). The scoring matrix used in Version 10 of the Wisconsin Genetics Software Package is BLOSUM62 (see Henikoff and Henikoff, *Proc. Natl. Acad. Sci* USA 89:10915, 1989).

Alignments using these programs can be performed using the default parameters. The CLUSTAL program is well described by Higgins et al, *Gene* 73:237-244, 1988; Higgins et al, *CABIOS* 5:151-153, 1989; Corpet et al, *Nucleic Acids Res.* —Vol. 6:10881-90, 1988; Huang et al, *CABIOS* 8:155-65, 1992; and Pearson et al, *Meth. Mol. Biol.* 24:307-331, 1994. The ALIGN and the ALIGN PLUS programs are based on the algorithm of Myers and Miller (1988) supra. A PAM 120 weight residue table, a gap length penalty of 12, and a gap penalty of four can be used with the ALIGN program when comparing amino acid sequences. The BLAST programs of Altschul et al, *J. Mol. Biol.* 215:403, 1990 are based on the algorithm of Karlin and Altschul 1990 supra. BLAST nucleotide searches can be performed with the BLASTN program, score=100, word length=12, to obtain nucleotide sequences homologous to a nucleotide sequence encoding a protein of the embodiments. BLAST protein searches can be performed with the BLASTX program, score=50, word length=3, to obtain amino acid sequences homologous to a protein or polypeptide of the embodiments. To obtain gapped alignments for comparison purposes, Gapped BLAST (in BLAST 2.0) can be utilized as described in Altschul et al, *Nucleic Acids Res.* 25:3389, 1997. Alternatively, PSI-BLAST (in BLAST 2.0) can be used to perform an iterated search that detects distant relationships between molecules. See Altschul et al 1997 supra. When utilizing BLAST, Gapped BLAST, PSI-BLAST, the default parameters of the respective programs (e.g., BLASTN for nucleotide sequences, BLASTX for proteins) can be used. See the web site for the National Center for Biotechnology Information on the World Wide Web. Alignment may also be performed manually by inspection.

Unless otherwise stated, sequence identity/similarity values provided herein refer to the value obtained using the Vector NTI program with default parameters, or any equivalent program. By "equivalent program" is intended any sequence comparison program that, for any two sequences in question, generates an alignment having identical nucleotide or amino acid residue matches and an identical percent sequence identity when compared to the corresponding alignment generated by Vector NTI (Invitrogen).

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, at least 80%, at least 90%, or at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, 70%, 80%, 90%, and at least 95%. Reference to "at least 70%" includes 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100% identity or similarity.

Another indication that nucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The *Elaeis* TCTP promoter sequence disclosed herein, as well as variants and fragments thereof, are useful for genetic engineering of plants, e.g. for the production of a transformed or transgenic plant, to express a phenotype of interest. As used herein, the terms "transformed plant" and "genetically modified plant" refer to a plant that comprises within its genome a heterologous polynucleotide. It includes an initially modified plant as well as its progeny which carry the same genetic modification. Generally, the heterologous polynucleotide is stably integrated within the genome of a genetically modified or transformed plant such that the polynucleotide is passed on to successive generations. The heterologous polynucleotide may be integrated into the genome alone or as part of a recombinant DNA construct. It is to be understood that as used herein the terms "genetically modified" and "transgenic" includes any cell, cell line, callus, tissue, plant part, or plant the genotype of which has been altered by the presence of heterologous nucleic acid including those transgenics initially so altered as well as those created by sexual crosses or asexual propagation from the initial transgenic. "Genetically modified" and "transgenic" as used herein do not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation. A transgenic "event" is produced by transformation of plant cells with a heterologous DNA construct, including a nucleic acid DNA construct that comprises a transgene of interest, the regeneration of a population of plants resulting from the insertion of the transgene into the genome of the plant, and selection of a particular plant characterized by insertion into a particular genome location. An event is characterized phenotypically by the expression of the transgene. At the genetic level, an event is part of the genetic makeup of a plant. The term "event" also refers to progeny produced by a sexual outcross between the transformant and another variety that include the heterologous DNA.

As used herein, the term "plant" includes reference to whole plants, plant organs (e.g., leaves, stems, roots, etc.), seeds, plant cells, and progeny of same. Parts of transgenic plants are to be understood within the scope of the embodiments to comprise, for example, plant cells, protoplasts, tissues, callus, embryos as well as flowers, stems, fruits, ovules, leaves, or roots originating in transgenic plants or their progeny previously transformed with a DNA molecule of the embodiments, and therefore consisting at least in part of transgenic cells. As used herein, the term "plant cell" includes, without limitation, seeds suspension cultures, embryos, meristematic regions, callus tissue, leaves, roots, shoots, gametophytes, sporophytes, pollen, and microspores. The class of plants that can be used in the methods disclosed herein is generally as broad as the class of higher plants amenable to transformation techniques, including both monocotyledonous and dicotyledonous plants.

The TCTP promoter sequence disclosed herein is useful in regulating expression of any heterologous nucleotide sequence in a host plant. Thus, the heterologous nucleotide sequence operably linked to the promoters disclosed herein may be a structural gene encoding a protein of interest. Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest for the embodiments include, for example, those genes involved in information, such as zinc fingers, those involved in communication, such as kinases, and those involved in housekeeping, such as heat shock proteins. More specific categories of transgenes, for example, include genes encoding proteins conferring resistance to abiotic stress, such as drought, temperature, salinity, and toxins such as pesticides and herbicides, or to biotic stress, such as attacks by fungi, viruses, bacteria, insects, and nematodes, and development of diseases associated with these organisms. Various changes in phenotype are of interest including modifying expression of a gene in a plant, altering a plant's pathogen or insect defense mechanism, increasing the plant's tolerance to herbicides, altering plant development to respond to environmental stress, and the like. The results can be achieved by providing expression of heterologous or increased expression of endogenous products in plants. Alternatively, the results can be achieved by providing for a reduction of expression of one or more endogenous products, particularly enzymes, transporters, or cofactors, or affecting nutrients uptake in the plant. These changes result in a change in phenotype of the transformed plant. It is recognized that any gene of interest can be operably linked to the promoter sequences of the embodiments and expressed in a plant.

A DNA construct comprising one of these genes of interest can be used with transformation techniques, such as those described below, to create disease or insect resistance in susceptible plant phenotypes or to enhance disease or insect resistance in resistant plant phenotypes. Accordingly, the embodiments encompass methods that are directed to protecting plants against fungal pathogens, bacteria, viruses, nematodes, insects, and the like. By "disease resistance" is intended that the plants avoid the harmful symptoms that are the outcome of the plant-pathogen interactions.

Disease resistance and insect resistance genes such as lysozymes, cecropins, maganins, or thionins for antibacterial protection, or the pathogenesis-related (PR) proteins such as glucanases and chitinases for anti-fungal protection, or *Bacillus thuringiensis* endotoxins, protease inhibitors, collagenases, lectins, and glycosidases for controlling nematodes or insects are all examples of useful gene products.

Genes encoding disease resistance traits include detoxification genes, such as against fumonisin (U.S. Pat. No. 5,792,931) avirulence (avr) and disease resistance (R) genes (Jones et al, *Science* 266:789, 1994; Martin et al, *Science* 262:1432, 1993; Mindrinos et al, *Cell* 78:1089, 1994); and the like. The TCTP promoter of the embodiments may be used to express disease resistance genes in a constitutive manner to prevent disease pathogens that typically infect plants.

The TCTP promoter of the present invention may also be used to express genes in a root-preferred manner which may include, for example, insect resistance genes directed to those insects which primarily feed on the roots. Such insect resistance genes may encode resistance to pests that have great yield drag such as various species of rootworms, cutworms, and the like. Such genes include, for example, *Bacillus thuringiensis* toxic protein genes (U.S. Pat. Nos. 5,366,892; 5,747,450; 5,737,514; 5,723,756; 5,593,881; and Geiser et al, *Gene* 48:109, 1986); lectins (Van Damme et al, *Plant Mol. Biol.* 24:825, 1994); and the like. Herbicide resistance traits may be introduced into plants by genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta, or other such genes known in the art. The bar gene encodes resistance to the herbicide basta, the nptll gene encodes resistance to the antibiotics kanamycin and geneticin, and the ALS gene encodes resistance to the herbicide chlorsulfuron.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al, *J. Bacteriol.* 170:5837-5847, 1988) facilitate expression of polyhyroxyalkanoates (PHAs).

Agronomically important traits that affect quality of palm oil products, such as levels and types of oils, saturated and unsaturated, quality and quantity of essential amino acids, levels of cellulose, starch, and protein content can be genetically altered using the methods of the present invention. Modifications include increasing content of oleic acid, saturated and unsaturated oils, increasing levels of lysine and sulfur, providing essential amino acids, and modifying starch.

Exogenous products include plant enzymes and products as well as those from other sources including prokaryotes and other eukaryotes. Such products include enzymes, cofactors, hormones, and the like.

Examples of other applicable genes and their associated phenotype include the gene that encodes viral coat protein and/or RNA, or other viral or plant genes that confer viral resistance; genes that confer fungal resistance; genes that confer insect resistance; genes that promote yield improvement; and genes that provide for resistance to stress, such as dehydration resulting from heat and salinity, toxic metal or trace elements, or the like.

The heterologous nucleotide sequence operably linked to the *Elaeis* TCTP promoter and its related biologically active fragments or variants disclosed herein may be an antisense sequence for a targeted gene. The terminology "antisense DNA nucleotide sequence" is intended to mean a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired phenotypic response. Modifications of the antisense sequences may be made as long as the sequences hybridize to and interfere with expression of the corresponding mRNA. In this manner, antisense constructions having 70%, 80%, 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used. Thus, the promoter sequences disclosed herein may be operably linked to antisense DNA sequences to reduce or inhibit expression of a native protein in the plant. "RNAi" refers to a series of related techniques to reduce the expression of genes (See for example U.S. Pat. No. 6,506,559). Older techniques referred to by other names are now thought to rely on the same mechanism, but are given different names in the literature. These include "antisense inhibition," the production of antisense RNA transcripts capable of suppressing the expression of the target protein, and "co-suppression" or "sense-suppression," which refer to the production of sense RNA transcripts capable of suppressing the expression of identical or substantially similar foreign or endogenous genes (U.S. Pat. No. 5,231,020, incorporated herein by reference). Such techniques rely on the use of constructs resulting in the accumulation of double stranded RNA with one strand complementary to the target gene to be silenced. The TCTP promoter sequence of the embodiments, and its related biologically active fragments or variants disclosed herein, may be used to drive expression of constructs that will result in RNA interference including microRNAs and siRNAs.

In one embodiment of the present invention, DNA constructs comprise a transcriptional initiation region comprising one of the promoter nucleotide sequences disclosed herein, or variants or fragments thereof, operably linked to a heterologous nucleotide sequence whose expression is to be controlled by the inducible promoter of the embodiments. Such a DNA construct is provided with a plurality of restriction sites for insertion of the nucleotide sequence to be under the transcriptional regulation of the regulatory regions. The DNA construct may additionally contain selectable marker genes.

The DNA construct includes in the 5'-3' direction of transcription, a TCTP promoter, a heterologous nucleotide sequence of interest (or means for insertion of such a heterologous sequence), a translational termination region and, optionally, a transcriptional termination region functional in the host organism. The regulatory regions other than the TCTP promoter (i.e., transcriptional regulatory regions, and translational termination regions) and/or the heterologous polynucleotide of the embodiments may be native/heterologous to the host cell or to each other. As used herein, "heterologous" in reference to a sequence is a sequence that originates from a species other than *Elaeis*, or, if from *Elaeis* species, is substantially modified from its native form in composition and/or genomic locus by deliberate human intervention. For example, a promoter operably linked to a heterologous polynucleotide is from *Elaeis* species different from the species from which the polynucleotide was derived, or, if from the same/analogous *Elaeis* species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the plant host, or may be derived from another source (i.e., foreign or heterologous) to the promoter, the polynucleotide of interest, the host, or any combination thereof. Convenient termination regions are available from the Ti-plasmid of *A. tumefaciens*, such as the octopine synthase and nopaline synthase termination regions.

The DNA construct comprising a promoter sequence of the embodiments operably linked to a heterologous nucleotide sequence may also contain at least one additional nucleotide sequence for a gene to be co-transformed into the organism. Alternatively, the additional sequence(s) can be provided on another DNA construct.

Where appropriate, the heterologous nucleotide sequence whose expression is to be under the control of the TCTP promoter and any additional nucleotide sequence(s) may be optimized for increased expression in the transformed plant. That is, these nucleotide sequences can be synthesized using plant preferred codons for improved expression. Methods are available in the art for synthesizing plant-preferred nucleotide sequences. See, for example, U.S. Pat. Nos. 5,380,831 and 5,436,391, and Murray et al, *Nucleic Acids Res.* 17:477-498, 1989, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The DNA constructs may additionally contain 5' leader sequences. Such leader sequences can act to enhance translation.

The DNA constructs of the embodiments can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA. It is recognized that to increase transcription levels enhancers may be utilized in combination with the promoter regions of the embodiments. Enhancers are known in the art and include the SV40 enhancer region, the 35S enhancer element, and the like.

In preparing the DNA construct, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites. Restriction sites may be added or removed, superfluous DNA may be removed, or other modifications of the like may be made to the sequences of the embodiments. For this purpose, in vitro mutagenesis, primer repair, restriction, annealing, re-substitutions, for example, transitions and transversions, may be involved. Reporter genes or selectable marker genes may be included in the DNA constructs. Examples of suitable reporter genes known in the art can be found in, for example, Jefferson et al. *In Plant Molecular Biology Manual*, ed. Gelvin et al. (Kluwer Academic Publishers):1-33, 1991; DeWet et al, *Mol. Cell. Biol.* 7:725-737, 1987; Goff et al, *EMBO J.* 0:2517-2522, 1990; Kain et al, *BioTechniques* 79:650-655, 1995; and Chiu et al, *Current Biology* 6:325-330, 1996.

Selectable marker genes for selection of transformed cells or tissues can include genes that confer antibiotic resistance or resistance to herbicides. Examples of suitable selectable marker genes include, but are not limited to, genes encoding resistance to chloramphenicol (Estrella et al, *EMBO J.* 2:987-992, 1983); methotrexate (Estrella et al, *Nature* 303:209-213, 1983; Meijer et al, *Plant Mol. Biol.* 16:807-820, 1991); hygromycin (Waldron et al, *Plant Mol. Biol.* 5:103-108, 1985; Zhijian et al, *Plant Science* 708:219-227, 1995); streptomycin (Jones et al, *Mol. Gen. Genet.* 270:86-91, 1987); spectinomycin (Bretagne-Sagnard et al, *Transgenic Res.* 5:131-137, 1996); bleomycin (Hille et al, *Plant Mol. Biol.* 7:171-176, 1990); sulfonamide (Guerineau et al, *Plant Mol. Biol.* 75:127-136, 1990); bromoxynil (Stalker et al, *Science* 242:419-423, 1988); glyphosate (Shaw et al, *Science* 233:478-481, 1986); phosphinothricin (DeBlock et al, *EMBO J.* 6:2513-2518, 1987).

Other genes that could serve utility in the recovery of transgenic events but might not be required in the final product would include, but are not limited to, examples such as GUS (b-glucuronidase; Jefferson, *Plant Mol. Biol. Rep.* 5:387, 1987 (green fluorescent protein; Chalfie et al, *Science* 263:802, 1994), luciferase (Riggs et al, *Nucleic Acids Res.* 75(19):8115, 1987 and Luehrsen et al, *Methods Enzymol.* 276:397-414, 1992), and the maize genes encoding for anthocyanin production (Ludwig et al, *Science* 247:449, 1990).

The nucleic acid molecules of the embodiments are useful in methods directed to expressing a nucleotide sequence in a plant. This may be accomplished by transforming a plant cell of interest with a DNA construct comprising a promoter identified herein, operably linked to a heterologous nucleotide sequence, and regenerating a stably transformed plant from said plant cell. The methods of the embodiments are also directed to inducibly expressing a nucleotide sequence in a plant. Those methods comprise transforming a plant cell with a DNA construct comprising a promoter identified herein that initiates transcription in a plant cell in an inducible manner, operably linked to a heterologous nucleotide sequence, regenerating a transformed plant from said plant cell, and subjecting the plant to the required stimulus to induce expression. The DNA construct comprising the particular promoter sequence of the embodiments operably linked to a nucleotide sequence of interest can be used to transform any plant. In this manner, genetically modified, i.e. transgenic or transformed, plants, plant cells, plant tissue, seed, root, and the like can be obtained.

Plant species suitable for genetic manipulation other than *Elaeis* sp. include, but are not limited to, corn (*Zea mays*), *Brassica* sp. (e.g., *B. napus, B. rapa, Bjuncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), oats (*Avena* spp.), sunflower (*Helianthus annuus*), safflower (*Carthamus tinctorius*), wheat (*Triticum aestivum*), barley (*Hordeum* spp.), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), onion (*Allium* spp.), dates (*Phoenix* spp.), vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the embodiments include, for example, pines such as loblolly pine (*Pinus* taeda), slash pine (*Pinus elliotii*), ponderosa pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

As used herein, "vector" refers to a DNA molecule such as a plasmid, cosmid, or bacterial phage for introducing a nucleotide construct, for example, an expression cassette, into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance, or ampicillin resistance.

The methods of the present invention involve introducing a nucleotide construct into a plant. As used herein "introducing" is intended to mean presenting to the plant the nucleotide construct in such a manner that the construct gains access to the interior of a cell of the plant. The methods of the embodiments do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods. A "stable transformation" is one in which the nucleotide construct introduced into a plant integrates into the genome of the plant and is capable of being inherited by progeny thereof. "Transient transformation" means that a nucleotide construct introduced into a plant does not integrate into the genome of the plant. The nucleotide constructs of the embodiments may be introduced into plants by contacting plants with a virus or viral nucleic acids. Generally, such methods involve incorporating a nucleotide construct of the embodiments within a viral DNA or RNA molecule. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367, and 5,316,931; herein incorporated by reference.

Transformation protocols as well as protocols for introducing nucleotide sequences into plants may vary depending on the type of plant or plant cell, i.e., monocotyledon or dicotyledon, targeted for transformation. Suitable methods of introducing nucleotide sequences into plant cells and subsequent insertion into the plant genome include microinjection (Crossway et al, *Biotechniques* 4:320-334, 1986), electroporation (Riggs et al, *Proc. Natl. Acad. Sci. USA* 83:5602-5606, 1986), *Agrobacterium*-mediated transformation (U.S. Pat. Nos. 5,981,840 and 5,563,055), direct gene transfer (Paszkowski et al, *EMBO J.* 3:2717-2722, 1984), and ballistic particle acceleration (see, for example, U.S. Pat. Nos. 4,945,050; 5,879,918; 5,886,244; 5,932,782; Tomes et al, In Plant Cell, Tissue, and Organ Culture: Fundamental Methods, ed. Gamborg and Phillips (Springer-Verlag, Berlin), 1995; and McCabe et al, Biotechnology 6:923-926, 1988).

The cells that have been transformed may be grown into plants in accordance with conventional ways. See, for example, McCormick et al, *Plant Cell Reports* 5:81-84, 1986. These plants may then be grown, and crossed with the same transformed strain or different strains, and the resulting hybrid which expresses the desired phenotypic characteristic. Two or more generations may be grown to ensure that inducible expression of the desired phenotypic characteristic is stably maintained and inherited and then seeds or plantlets harvested to ensure expression of the desired phenotypic characteristic has been achieved. Thus as used herein, "transformed seeds" or "transformed plants" refers to seeds and plants that contain the nucleotide construct stably integrated into the plant genome.

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, *In: Methods for Plant Molecular Biology*, (Eds.), Academic Press, Inc., San Diego, Calif., 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. In one embodiment, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the embodiments containing a desired polypeptide is cultivated using methods well known to one skilled in the art.

The present invention provides vectors, cells, and plants comprising the *Elaeis* TCTP promoter operably linked to a heterologous DNA sequence. The *Elaeis* TCTP promoter can also be used to screen for agonists and antagonists of the TCTP promoter. For example, a reporter gene can be operably linked to an *Elaeis* TCTP promoter and expressed as a transgene in a plant. Compounds to be tested are added and reporter gene expression is measured to determine the effect on promoter activity.

The present invention is further described in the following non-limiting Examples.

EXAMPLE 1

Identifying a Constitutive Gene from Oil Palm

Isolation of total RNA

Total RNA from oil palm green leaves was isolated using the method of Zeng and Yang, Plant. Mol. Biol. Rep. 20:417a-417c, 2002.

Reverse Northern Analysis

Reverse northern dot blot was performed as the manufacturers instruction (Bio-Dot® Microfiltration Apparatus, BIO-RAD). Wells of dot blot were rinsed with 300 µl 2×SSC (3M NaCl, 300 mM tri-sodium citrate, pH 7.0). About 200 µg of the amplicons derived from amplification of cDNA via PCR was added with 0.4N NaOH, then denatured by boiling for 10 min and chill in ice immediately. About 100 µl of the preparation were dot blotted onto nylon membrane and aspirated through under vacuum. Then, the wells were rinsed twice with 300 µl 2×SSC, sucked through the manifold under vacuum and briefly air-dried. The membrane was UV crossed-link and probed with [$\alpha$-$^{32}$P] cDNA. The cDNA was prepared by reverse transcribed of 3 µg total RNA from oil palm tissues according to First Strand cDNA synthesis kit (Invitrogen) and had been radiolabeled with [α-$^{32}$P] according to the Megaprime™ DNA Labeling System manual (Amersham Life Science). Hybridization was carried out with standard reagents, according to standard techniques (Sambrook et al, *Molecular cloning: a laboratory manual* 2$^{nd}$ Ed., Cold Spring Harbor Laboratory Press, USA, 1989). Blots were exposed to Kodak XAR-5 film for 3 days.

Northern Analysis

About 15 μg of total RNA from various oil palm tissues were denatured in RNA loading buffer containing 48% v/v formamide, 6.4% v/v formaldehyde, 1×MOPS buffer, 5.3% v/v glycerol and 0.02% w/v Bromophenol blue. The mixture was denatured by heating for 10 minutes at 65° C. followed by immediate cooling. Denatured total RNA was separated on 1% v/v formaldehyde gel using 1×MOPS Buffer (pH 7.0) as electrophoresis buffer. Transfer to nylon membrane (Hybond N$^+$ Amersham) was carried out using capillary transfer method. Prehybridization and hybridization were carried out in the same solution. Prehybridization was carried out in a hybridization bottle (FHB11, Techne) containing 30 ml hybridization solution (5×SSC, 5× Denhartds, 0.5% w/v SDS and 100 μg/ml denatured herring sperm DNA). The prehybridization was carried out at 65° C. for at least 2 hours in Hybridiser HB-1D (Techne) hybridization oven. After prehybridization, denatured labeled DNA probe was pipetted directly into the hybridization buffer without touching the membrane. The hybridization was performed at 65° C. for overnight. After the hybridization completed, membranes were removed from the bottle and washed in 1×SSC, 0.1% w/v SDS for 15 minutes at room temperature. The membranes were then washed twice for 30 minutes at 65° C. in 0.1×SSC and 0.1% w/v SDS. After the washing, the membranes were placed in autoradiography cassette and exposed to X-ray film (Kodak) with an intensifying screen at −80° C. for a week.

EXAMPLE 2

Isolation of Constitutive Promoter

Isolation of Total DNA

Extraction of genomic DNA was carried out according to Doyle and Doyle, *Phytochemical Bulletin* 19:11-15, 1987 with some modifications.

PCR Amplification

The promoter region of selected gene was isolated by polymerase chain reaction (PCR) using a pair of specific primers from oil palm genomic DNA. The genomic sequences was analyzed using Orion and EST databases (Genomic Group, MPOB). The PCR reaction were consisted of 40 μl dH$_2$0, 5 μl 10× Advantage 2 PCR buffer, 1 μl 10 mM dNTP, 1 μl 10 μM forward and reverse primers and 1 μl Advantage Advantage 2 Polymerase Mix. Amplification was performed on either PTC 100 or PTC 200 Programmable Thermal Control (MJ Research, Inc) in 40 cycles of 94° C. for 30 sec for denaturation, 60° C. for 30 sec for annealing and 72° C. for 2 min for extension. A final extension at 72° C. for 7 min was added after the last cycles.

Cloning the DNA Fragment

The PCR product was analyzed by agarose gel electrophoreses and fragment obtained was purified using QIAquick Gel Extraction Kit (QIAGEN) as described in the manufacturer's manual. The purified PCR product was ligated into PCRII-topo vector (TOPO TA Cloning Kit, Invitrogen Life Technologies) for further manipulation. Ligation reactions were carried out in mixtures of 3 μl (about 30 ng) of purified PCR product, 1 μl salt solution (1.2 M NaCl, 0.06 M MgCl$_2$) and 1 μl (10 ng) vector plasmid. Sterilized water was added to the final volume of 6 μl. The mixture was incubated at room temperature for 5 to 10 minutes. The mixture was then clone into One Shot® Chemically Competent *E. coli* following the manufacturer protocol.

DNA Sequencing for Clone Verification

Plasmid DNA for sequencing was prepared using Plasmid Mini Preparation Kit (QIAGEN) according to the manufacturer protocol. Representative clones were sequenced using automated DNA sequencer (ABI PRISM Model 377 Version 3.4). Analysis of DNA sequences was carried out using VectorNTI software (Invitrogen). The analysis included the removal of unreadable and vector sequences, sequence alignment, ORE identification and contig analysis and assembly. DNA and protein homology search against the GenBank databases was performed using BLAST 2.0 (Altschul et al, 1997 supra). The location of transcription start site (TSS) was identified using EST and Orion databases (Genomic Group, MPOB). Identification for cis-acting regulatory elements were performed using MOTIF search at the publicly accessible databases. The databases are Softberry (available on the worldwide web at softberry.com/berry.phtml), PLACE (available on the worldwide web at dna.affr.go.jp/PLACE) and PLANTCARE (available on the worldwide web at bioinformatics.psb.ugent.be/webtools/plantcare/html/).

EXAMPLE 3

Evaluation of Promoter Activity

Construction of Transformation Vector

The promoter activity can be determined through transient expression studies using a reporter gene such as GUS. In this study, the promoter region was cloned into pBI221 plasmid, behind the gusA gene to replace the Cauliflower Mosaic virus (CaMV)35S promoter. Plasmid pBI221 and promoter fragment (in PCRII-topo vector) were digested with appropriate restriction enzymes. Digestions were carried out in 100 μl reaction mixtures containing 20 μl DNA, 1× buffer and 5 μl (10 units) restriction enzymes. The digestion mixtures were incubated at 37° C. for overnight. The mixtures were analyzed by gel agarose electrophoresed and fragment obtained was purified using QIAquick Gel Extraction kit (QIAGEN). Ligation reaction was carried out in mixture containing of 1 μl of purified pBI221 vector plasmid, 1× T4 ligation buffer, 2 μl T4 ligase and 5 μl purified DNA insert. The sterile water was added to the final volume of 20 μl and mixture was incubated at 16° C. for overnight. The mixture was cloned into One Shot® Chemically Competent *E. coli* competent cells following the manufacturer protocol and screening for clones containing recombinant plasmid was carried out by restriction analysis for insert confirmation.

Preparation of Target Material for Transformation

Oil palm tissues such as embryogenic calli, embryoid, immature embryo, young leaflet from mature palm (YLMP), green leaves, stem, mesocarp 9 WAA and tobacco leaves were cultured on agar solidified medium containing Murashige and Skoog, *Physiol. Plant.* 15:473-97, 1962 (MS) macro and micronutrient supplemented with 1 mg litre$^{-1}$ napthalene acetic acid NAA and 30 g/L sucrose. The medium was adjusted to pH 5.7 and autoclaved at 121° C. for 15 minutes. Besides, mesocarps were sterilized in 20% v/v Clorox for 20 min, followed by rinsing three times with sterile distilled water before cultured. All explants except for embryogenic culture, embryoid and immature embryo were cut into 5 mm×5 mm disks before placing onto MS medium. For immature embryo, the explant was cultured for a week before bombardment. The other tissues were incubated in the dark at 28° C., 24 hr before bombardment.

Bombardment of Oil Palm Tissues

Particle bombardment of plasmid DNA was employed using Bio-Rad PDS-1000 He biolistic particle delivery system (Bio-Rad, Hercules, Calif. USA). To each aliquot of 100 μl gold particles, 20 μg DNA, 100 μl 2.5 M $CaCl_2$, and 40 μl 0.1 M Spermidine were added in order, with continuous vortexing. The vortexing was continued for 3 minutes followed by centrifugation at 10,000 rpm for 10 seconds. The supernatant was removed as much as possible and the particles were washed twice with 500 μl 100% v/v ethanol, followed by mixing, and centrifugation at 10,000 rpm for 60 seconds. Finally, the DNA coated gold particles were resuspended in 120 μl absolute ethanol. For each bombardment, 6 μl of DNA coated gold particles were dispensed onto the centre of a macrocarrier and dried under a sterile condition. The target tissues were placed in the centre of an agar containing petri dish. Transformation was carried out using the following parameters: bombardment pressure at 1100 psi; macrocarrier to stopping screen distance at 6 mm; target plates distance at 6 cm; chamber vacuum at 26 inch Hg (Parveez, 1998 supra). The bombarded tissues were incubated in the dark at 28° C., 48 hours before GUS histochemical analysis.

GUS Histochemical Assay

The GUS assay buffer (0.1 M $NaPO_4$ buffer pH7.0, 0.5 mM K-Ferricyanide, 0.5 mM K-Ferrocyanide, 0.01 M EDTA, 1 mg/ml X-gluc (5-Bromo-4-Chloro-3-Indolyl-β-D-glucuronide), 1 μl/ml Triton-X and 20% v/v methanol (v/v)) (Klein et al, *Nature* 327:70-73, 1988) was filter sterilized and stored at -20° C. in the dark. Two days after bombardment, the tissues were stained overnight (20 hr) at 37° C. with GUS buffer. For green tissues, pos-incubation treatment was performed by soaked the tissues in fresh 70% v/v ethanol for 5 times and incubated at 37° C., or until the plant tissues are light green or clear. The chlorophyll is extracted into the ethanol making easier to see the blue staining of the plant tissue. Blue spots were scored optically using a Nikon UFX-DX system.

EXAMPLE 4

Identification of Constitutively Expressing Gene from Oil Palm

Figure 2:
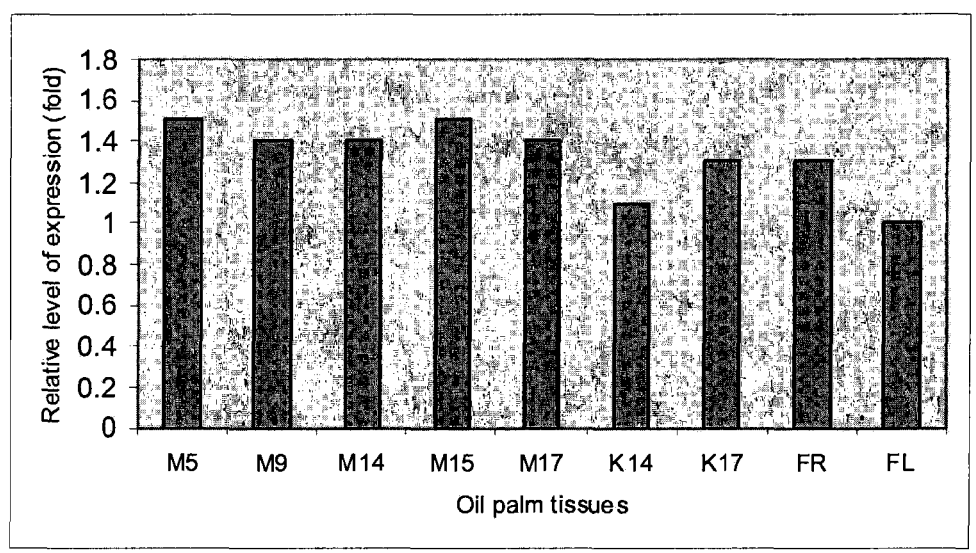
FIG. 2 is a graphical representation showing expression of pOP-RD00041 cDNA in various tissues of oil palm through reverse northern analysis. M5) mesocarp 5 week after anthesis (WAA); M9) mesocarp 9 WAA; M14) mesocarp 14 WAA; M15) mesocarp 15 WAA; M17) mesocarp 17 WAA; K14) kernel 14 WAA; K17) kernel 17 WAA; FR) frond and FL) flower.
Figure 3:
FIG. 3 is a photographic representation of a northern analysis for pOP-RD00041 cDNA. (a) Each lane contain 15 μg of total RNA prepared from different tissues of oil palm. Lane 1-4: mesocarp at 5, 14, 17, 20 WAA; Lane 5-6: kernel at 14, 17 WAA; Lane 7: flower; Lane 8: frond; Lane 9: embryoid; Lane 10: root; Lane 11: plantlet and Lane 12: young leaf. Equal loading of RNA was verified with 28S ribosomal DNA. (b) Arrow indicates the size of transcript.

The identification of a constitutively expressing gene in oil palm and isolation of its endogenous promoter towards development of construct ideal for constitutive expression of transgene in oil palm is provided. The gene was identified through screening the expression pattern of 73 EST clones by using reverse northern analysis (FIG. 1). In this study, a cDNA clone, namely pOP-RD00041 showed the presence of strong signal in all tissues tested. The cDNA was expressed in all tissues tested with ranged of about 1.0-1.5 fold (FIG. 2). The constitutive status of this gene was further validated using northern analysis. The transcript of this gene was highly expressed and approximately at the same levels in all tissues tested including mesocarps, kernels, young leaves, root, flower, frond, embryoid and plantlet (FIG. 3).

Based on database search, the cDNA was found to code translationally control tumor protein (TCTP) gene. This gene contains 507 nucleotide residues which code for 168 amino acids. It also contains 175 by of 3'-end non-coding region sequence including its poly A+ tail (SEQ ID NO: 1). The coding region was deposited to GenBank database by Genomic Group, MPOB (Accession No. EU 284975).

A number of studies had been shown that this gene is ubiquitously expressed and distributed protein in eukaryotes (Boomer and Thiele, Int. *J. Biochem Cell Biol.* 36:379-385, 2004). Although the function of this is remain elusive, TCTP has found to have a role as one of growth related protein in various organism. This gene related to diverse cellular processes, for example apoptosis, microtubule organization, or ion homeostatis and also associates to several interacting protein such as polo kinase, tubulin and $Na^+/K^+$-ATPase. Recent study have also shown that TCTP was identified as an important component of the TOR (target of rapamycin) signaling pathway, which known as the major regulator of cell growth (Berkowitz et al, *The Plant Cell* 20:3430-3447, 2008). Although this gene was initially found in cancerous mammalian tissues, there is interesting evidence indicated that TCTP is not a tumor-specific protein. In fact, its expression has been found in healthy animals and plants tissues (Kang et al, U.S. Pat. No. 6,518,484 B2, 2003). For example, high expression of TCTP transcript was detected in all parts of plants examined such as in *Arabidopsis* (Berkowitz et al, 2008 supra), *Hevea brasiliens* (Shin and Han, *Plant Physiol* 119:363, 1999), *Pharbitis* (Sage-Ono et al, *Plant Cell Physiol.* 39:357-360, 1998) and *Pisum sativum* (Woo and Hawes, *Plant Mol. Biol.* 35:1045-1051, 1997). This gene was also found to be very stable against heat, pH, ionic strength and even against protease, suggesting that it has a very compact globular structure (Kang et al, 2003 supra).

A promoter of TCTP was isolated from *Arabidopsis* and it was found capable of driving high expression of transgene in transgenic plant (Kang et al, 2003 supra). As the oil palm mRNA was also highly abundant in all tissues tested which suggested that the promoter could be used to drive transgene expression in oil palm, or in another plant with high economic value.

EXAMPLE 5

Constitutive Promoter from Oil Palm

Figure 4:
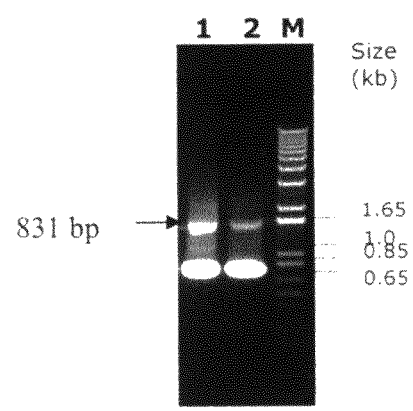
FIG. 4 is a photographic representation of amplification of the *Elaeis* TCTP promoter by PCR amplification of oil palm genomic DNA. Lane M: 1 Kb plus DNA ladder; Lane 1-2: PCR products. Arrow indicates the size obtained.

PCR amplification was carried out to amplify promoter region of TCTP gene. About 831 by PCR product containing the promoter including a part of coding region of the TCTP gene was successfully obtained (FIG. 4). The purified PCR product was ligated into PCRII-topo vector (TOPO TA Cloning Kit, Invitrogen Life Technologies) for further manipulation. The recombinant plasmid was designated as pGWTCTP. The DNA sequences were analysed using available databases online, including NCBI, Softberry, PlantCare, PLACE and VNTI software. Detailed analysis showed that a total 802 residues starting from its translational start site were identified as a part of the TCTP promoter including its 5' untranslated region. This fragment also consists of a part of the coding region with size of about 29 bp. Detailed analysis by using Orion and EST databases developed by Genomic Group of MPOB, Malaysia, revealed that the location of the putative transcription start site was identified to start at nucleotide cytosine (C) which is 62 nucleotides upstream from translation initiation site of the gene. A potential TATA box sequence was identified at -47 upstream of transcription start site. However, neither CAAT box nor GC-rich element is identified at appropriate positions in the 5' untranslated region. This finding is in agreement to *Arabidopsis* TCTP promoter, which shown that the typical CAAT box or GC-rich element was also not be found in its promoter region (Kang et al. 2003). Computational analysis was used to identify features in gene architecture that contributed toward determining the expression level of the TCTP gene. Results indicated that TCTP promoter contains cis-acting elements or motifs that associated to light-responsive elements such as Gap box, GATA, GAG and TCT motif. Light-responsive element was also found in *Arabidopsis* TCTP promoter (Kang et al, 2003 supra). Previous study also suggested that TCTP has a role in light regulated growth in short day plant Japanese morning glory (Pharbitis nil cv. Violet). In this *Pharbitis* species, the TCTP mRNA increased during the dark treatment but the expression level decreased to undetectable level in light (Sage-Ono et at, 1998 supra). In addition, TCTP promoter also contains other interesting motifs such as cis-acting element involved in heat stresses (HSE) and MYB binding sites involved in drought inducibility (MYB). The presence of these motifs indicates the possible function of the gene in multiple hormonal pathways and its ability to respond to multiple environmental cues. In *Arabidopsis*, the expression of TCTP gene was further induced by 15% treatment which mimics the drought stressed condition in plants (Kang et al, 2003 supra). Interestingly, the promoter also contains 5'UTR Py-rich element which has been identified as cis-acting element that confers high transcription levels in pea. As conclusion, this finding clearly indicates that the TCTP promoter is controlled by synergism of multiple cis-acting regulatory elements to confer constitutive expression in plant growth and development. The cis elements found in the genomic sequence of TCTP are shown in FIG. 5.

EXAMPLE 6

Evaluation of Promoter Activity

Figure 6:
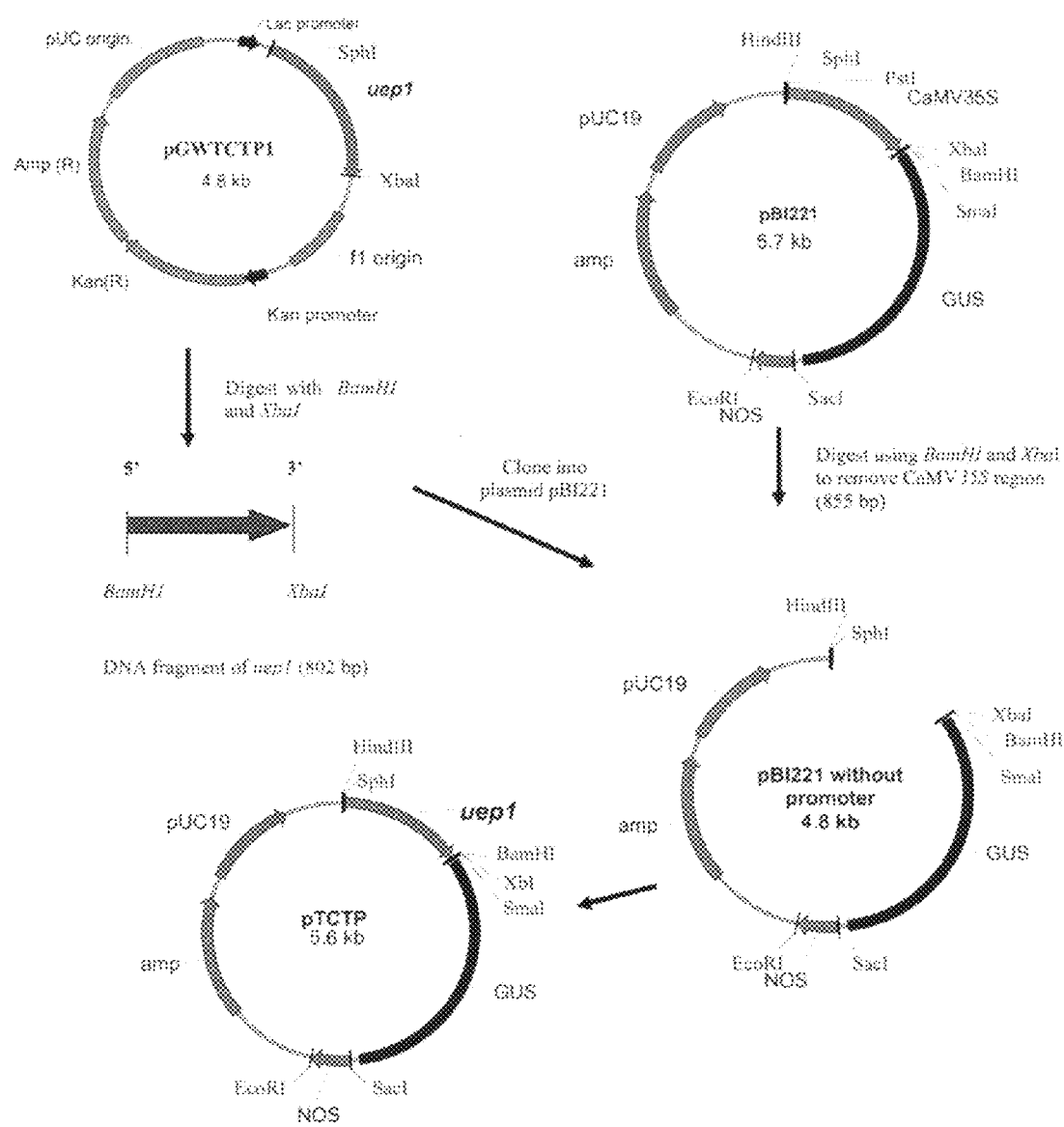
FIG. 6 is a diagrammatic representation of construction of pTCTP transformation vector. The pGWTCTPI was digested with Sphl and BamHl and TCTP promoter was cloned into pBI221 by removing the CaMV35S to generate pTCTP. The arrow indicates the orientation of each DNA fragment assembled.

Functional analysis study of the promoter was subsequently performed through construction of transformation vector containing gusA as a reporter gene and nos terminator under the control of TCTP promoter. In promoter analysis, the coding region, starting from translation start site should be removed from the fragment. Removing of translation start site is important to avoid undesired translation initiation from the TCTP gene and to ensure the expression of reporter genes occur from its own translational start codon. Promoter and its 5' untranslated region were amplified from plasmid pGWTCTP. The amplification was also used as means to introduce Sphl site flanking the 5' end and BamHI site flanking the 3' end. The purified PCR products were then ligated into PCRII-topo vector (TOPO TA Cloning Kit, Invitrogen Life Technologies) to form pGWTCTP 1 plasmid DNA. In this study, TCTP promoter was cloned into pB1221 transformation vector (Clontech, USA) by replacing the CaMV35S promoter to form a new transformation vector designated as pTCTP. The construction of pTCTP was carried out using plasmid DNA pGWTCTP1 as illustrated in FIG. 6.

A transient expression study by a histochemical GUS assay was performed to evaluate the activity of the promoter. The pTCTP vector that carries the TCTP promoter was bombarded into oil palm tissues including embryogenic calli, embryoid, young leaflet from mature palm (YLMP), green leaf, stem tissues (shoot tip), mesocarp and immature embryo. The ubil (plasmid pAHC25) and CaMV35S (original plasmid pBI221) which are known as strong monocot and dicot promoters, respectively, were included as controls. GUS activity was determined by counting the number of GUS-positive spots optically. The data collected were then summarized in the form of mean comparison and standard deviation as shown in Table 2. The result indicated that TCTP promoter functions as a constitutive promoter in oil palm plants (*Elaeis*), due to its ability to express GUS in all the tissues that was tested (FIG. 7). Interestingly, this promoter could also be used in dicots system as it capable of driving the expression of GUS in tobacco (FIG. 7). These results also indicated that although TCTP has high activity, the strength of this promoter was slightly lower than the controls in some tissues, particularly in YMLP and embryoid. Thus, in order to enhance the promoter effectiveness, modification of promoter by addition of first intron region behind the gus reporter gene is still on going. This strategy was found to successfully increase the strength of other constitutive promoters in monocotyledonous plants. This finding clearly suggests that the endogenous *Elaeis* TCTP promoter could be used as a crucial biotechnology tool for producing ubiquitous expression of transgenes in transgenic oil palm.

TABLE 2

Comparison of promoter strength on transient gusA gene expression and GUS activity in oil palm tissues two days after bombardment

| Promoter/ Construct | Mean (Standard Error) of GUS foci | | | | | | | |
|---|---|---|---|---|---|---|---|---|
| | EC | EM | YMLP | GL | MS | ST | IE | TB |
| Ubil/pAHC25 | 121.67 ± 17.68 | 568.8 ± 129.5 | 9166.6 ± 119.2 | 25.2 ± 6.72 | 6.7 ± 2.0 | 62.0 ± 27.7 | 170 ± 0.0 | 15 ± 11.0 |
| CaMV35S/ pBI221 | 100.33 ± 52.1 | 314.0 ± 56.5 | 3504.2 ± 133.3 | 7.6 ± 2.6 | 2.8 ± 0.6 | 85.7 ± 3.23.3 | — | 33 ± 9.71 |
| TCTP/pTCTP | 38.00 ± 19.01 | 183.33 ± 39.29 | 521.67 ± 94.53 | 24.50 ± 16.5 | 1 ± 0.0 | 54.0 ± 19.86 | 208.0 ± 77.0 | 26 ± 7.0 |

EC = Embryogenic callie
EM = Embryoid
YMLP = Young leaflet from mature palm
GL = Green leaf
MS = Mesocarp 9 WAA
ST = Stem (meristematic tissues)
IE = Immature embryo
T = Tobacco Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention claimed is:

1. A DNA construct comprising the nucleotide sequence set forth in SEQ ID NO:1 or the full length complement thereof operably linked to a heterologous nucleotide sequence of interest.

2. A plant cell having stably incorporated into its genome the DNA construct of claim 1.

3. The plant cell of claim 2, wherein said plant cell is from a monocot.

4. The plant cell of claim 3, wherein said monocot is a species of *Elaeis*.

5. The plant cell of claim 2, wherein said plant cell is from a dicot.

6. A plant having stably incorporated into its genome the DNA construct of claim 1.

7. The plant of claim 6, wherein said plant is a monocot.

8. The plant of claim 7, wherein said monocot is a species of *Elaeis*.

9. The plant of claim 6, wherein said plant is a dicot.

10. A genetically modified seed of the plant of claim 6, wherein the seed comprises the DNA construct.

11. The plant of claim 6, wherein the heterologous nucleotide sequence of interest encodes a gene product or a double-stranded RNA that confers resistance to a herbicide, resistance to a pest including a pathogenic agent or resistance to disease, or confers a modification to the levels or composition of lipid and non-lipid components of palm oil.

12. A method for expressing a nucleotide sequence in a plant, said method comprising introducing into a plant the DNA construct of claim 1.

13. The method of claim 12, wherein said plant is a monocot.

14. The method of claim 13, wherein said monocot is a species of *Elaeis*.

15. The plant cell of claim 12, wherein said plant is a dicot.

16. The method of claim 12, wherein the heterologous nucleotide sequence encodes a gene product or a double-stranded RNA that confers resistance to a herbicide, resistance to a pest including a pathogenic agent or resistance to disease, or confers a modification to the levels or composition of lipid and non-lipid components of palm oil.

17. A method for expressing a nucleotide sequence in a plant cell, said method comprising introducing into a plant cell the DNA construct of claim 1.

18. The method of claim 17, wherein said plant cell is from a monocot.

19. The method of claim 17, wherein said monocot is a species of *Elaeis*.

20. The plant cell of claim 17, wherein said plant cell is from a dicot.

21. The method of claim 17, wherein the heterologous nucleotide sequence encodes a gene product or a double-stranded RNA that confers resistance to a herbicide, resistance to a pest including a pathogenic agent or resistance to disease, or confers a modification to the levels or composition of lipid and non-lipid components of palm oil.

22. The method of claim 17, wherein expression of said heterologous nucleotide sequence alters a phenotype of said plant cell.

23. The method of claim 22, wherein the plant cell is a monocot.

24. The method of claim 23 wherein the monocot is *Elaeis*.

25. The method of claim 22, wherein said plant cell is from a dicot.

26. The method of claim 22, wherein the heterologous nucleotide sequence encodes a gene product or double-stranded RNA that confers resistance to a herbicide, resistance to a pest including a pathogenic agent or resistance to disease, or confers a modification to the levels or composition of lipid and non-lipid components of palm oil.

* * * * *

UNITED STATES PATENT AND TRADEMARK OFFICE
CERTIFICATE OF CORRECTION

PATENT NO. : 8,604,275 B2  
APPLICATION NO. : 12/779010  
DATED : December 10, 2013  
INVENTOR(S) : Ghulam Kadir et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 34 days.

Signed and Sealed this
Twenty-second Day of April, 2014

Michelle K. Lee
*Deputy Director of the United States Patent and Trademark Office*

SEQUENCE LISTING

<160> NUMBER OF SEQ ID NOS: 4

<210> SEQ ID NO 1
<211> LENGTH: 802
<212> TYPE: DNA
<213> ORGANISM: artificial sequence
<220> FEATURE:
<223> OTHER INFORMATION: Elaeis guineensis TCTP promoter

<400> SEQUENCE: 1

```
aagtcccgat tggatatttc atgagatatc aagatgagta tcatcttatg tgttaggata      60
ggatcatcca gtttaatcgg cacatcttga gatattttct tatctcaagt atccaaatga     120
gaggagatga tggtatatct tgtttcatta gaaaatgagg atggtacctt cttacaagat     180
ttaaagtctt ggacctaaag ttggatacct agataaagtg agtttgagga aattaaaatg     240
gagaaaaaaa tttatgagag aaattccata gatcctattc atattggcag ctacacttat     300
ttcttccaaa ttttttctct ctgttaacca taattcatgc agcctctcca ttatcttgca     360
tcgacactag agtaccgtgc aacatttta ttgtagtgtt atcattatcc tagcgtccaa      420
gaattggatt caaaaggcgt ctaagcccat ggtagtccat ccccgaactc gaaccagacc     480
atttagatta gatcggtttt ggatttgaga cctaatcata acaatccgat aagaatttgg     540
tcacctggac ttccggtgtg aacatctttg agatcagaat tcatctcgct gatcggacgg     600
accggaaaag agctcgtgtg aaactcgaac accaacgatg gactcaactg tagccagcga     660
caccccgctc gaaaccccaa attctctcgc ccatataaga tcctcgcggc cacctttta     720
gatccctctc tctcctgcct ccttcgcccg ctccttcgtc tattcggtca ccggggtta     780
gggtttgctc tttggaggaa tc                                              802
```

<210> SEQ ID NO 2
<211> LENGTH: 682
<212> TYPE: DNA
<213> ORGANISM: artificial sequence
<220> FEATURE:
<223> OTHER INFORMATION: Elaeis guineensis TCTP coding strand and 3' end

<400> SEQUENCE: 2

```
atgctcgtct accaggatct tctcacaggc gatgagcttt tgtcggactc atttccgtac      60
aaggaaatac acaatggtat gctgtgggaa gttgaaggaa agtgggtcat tcaaggagca     120
gtaaatgtcg acattggtgc aaacccttcc gccgaaggtg gtgaagaaga tgaaggagtt     180
gatgaccagg ctgttaaggt ggtcgatatt gtggatactt ttaggcttca ggagcaaccg     240
gcattcgata gaaacaatt tgtgaccttc atgaagagat atatcaaaaa tttgactcct     300
aaattggatg ccgagaagca ggagctattt aagaaacaca ttgagggagc taccaagttt     360
ttactttcaa agcttagtga cctgcaattt tttgtagggg agagtatgca cgatgatggg     420
tgcctagtct tgcatacta caaagatggt gcaactgatc caacattctt atattttgcc     480
tatgggctga aggaggtcaa atgctgaatt tacccgactc ctgatgagat gtgctgtaac     540
ttcagcttat ttatcattta ccccgttttg tgttgagtga gacgtggaag caatgcctta     600
actttaata tgattgagaa tttgactttt tctttgggat atttagttgg atcatttggt     660
gatattgatt tgattaaaaa aa                                              682
```

<210> SEQ ID NO 3
<211> LENGTH: 682
<212> TYPE: DNA

```
<213> ORGANISM: artificial sequence
<220> FEATURE:
<223> OTHER INFORMATION: Elaeis guineensis TCTP complementary strand of
      SEQ ID NO.2

<400> SEQUENCE: 3
tacgagcaga tggtcctaga agagtgtccg ctactcgaaa acagcctgag taaaggcatg      60
ttcctttatg tgttaccata cgacaccctt caacttcctt tcacccagta agttcctcgt     120
catttacagc tgtaaccacg tttgggaagg cggcttccac cacttcttct acttcctcaa     180
ctactggtcc gacaattcca ccagctataa cacctatgaa atccgaagt cctcgttggc      240 cgtaagctat tctttgttaa acactggaag tacttctcta tatagttttt aaactgagga     300
tttaacctac ggctcttcgt cctcgataaa ttctttgtgt aactccctcg atggttcaaa     360
aatgaaagtt tcgaatcact ggacgttaaa aaacatcccc tctcatacgt gctactaccc     420
acggatcaga aacgtatgat gtttctacca cgttgactag gttgtaagaa tataaaacgg     480
atacccgact tcctccagtt tacgacttaa atgggctgag gactactcta cacgacattg     540
aagtcgaata aatagtaaat ggggcaaaac acaactcact ctgcaccttc gttacggaat     600
tgaaaattat actaactctt aaacctgaaa agaaacccta taaatcaacc tagtaaacca     660
ctataactaa actaattttt tt                                              682

<210> SEQ ID NO 4
<211> LENGTH: 168
<212> TYPE: PRT
<213> ORGANISM: artificial sequence
<220> FEATURE:
<223> OTHER INFORMATION: Elaeis guineensis TCTP amino acid sequences

<400> SEQUENCE: 4

Met Leu Val Tyr Gln Asp Leu Leu Thr Gly Asp Glu Leu Leu Ser Asp
1               5                   10                  15

Ser Phe Pro Tyr Lys Glu Ile His Asn Gly Met Leu Trp Glu Val Glu
            20                  25                  30

Gly Lys Trp Val Ile Gln Gly Ala Val Asn Val Asp Ile Gly Ala Asn
        35                  40                  45

Pro Ser Ala Glu Gly Gly Glu Glu Asp Glu Gly Val Asp Asp Gln Ala
    50                  55                  60

Val Lys Val Val Asp Ile Val Asp Thr Phe Arg Leu Gln Glu Gln Pro
65                  70                  75                  80

Ala Phe Asp Lys Lys Gln Phe Val Thr Phe Met Lys Arg Tyr Ile Lys
                85                  90                  95

Asn Leu Thr Pro Lys Leu Asp Ala Glu Lys Gln Glu Leu Phe Lys Lys
            100                 105                 110

His Ile Glu Gly Ala Thr Lys Phe Leu Leu Ser Lys Leu Ser Asp Leu
        115                 120                 125

Gln Phe Phe Val Gly Glu Ser Met His Asp Asp Gly Cys Leu Val Phe
    130                 135                 140

Ala Tyr Tyr Lys Asp Gly Ala Thr Asp Pro Thr Phe Leu Tyr Phe Ala
145                 150                 155                 160

Tyr Gly Leu Lys Glu Val Lys Cys
                165
```